(12) United States Patent
Suh et al.

(10) Patent No.: US 7,973,168 B2
(45) Date of Patent: Jul. 5, 2011

(54) METALLIC COMPOUND AND ORGANIC ELECTROLUMINESCENCE DEVICE COMPRISING THE SAME

(75) Inventors: Dong-Hack Suh, Seongnam (KR); Jin-Soo Lim, Seoul (KR); Ji-Ho Kim, Seoul (KR); Sun-Hyun Choi, Suncheon (KR)

(73) Assignees: Samsung Electronics Co., Ltd. (KR); Industry—University Cooperation Foundation, Hanyang University (KR)

( * ) Notice: Subject to any disclaimer, the term of this patent is extended or adjusted under 35 U.S.C. 154(b) by 141 days.

(21) Appl. No.: 11/913,222

(22) PCT Filed: Jan. 8, 2007

(86) PCT No.: PCT/KR2007/000112
§ 371 (c)(1),
(2), (4) Date: Oct. 31, 2007

(87) PCT Pub. No.: WO2007/078183
PCT Pub. Date: Jul. 12, 2007

(65) Prior Publication Data
US 2009/0326236 A1     Dec. 31, 2009

(30) Foreign Application Priority Data
Jan. 6, 2006 (KR) .......................... 10-2006-0001822

(51) Int. Cl.
*C07F 15/00* (2006.01)
*H01J 1/63* (2006.01)
(52) U.S. Cl. .................... 548/103; 313/504; 428/917
(58) Field of Classification Search .................. None
See application file for complete search history.

(56) References Cited

U.S. PATENT DOCUMENTS
6,703,146 B1    3/2004  Sakaguchi et al.
2005/0287391 A1*  12/2005  Chang et al. ................. 428/690

FOREIGN PATENT DOCUMENTS
JP    2003077675    3/2003
JP    2003171659    6/2003
JP    2003264086    9/2003

OTHER PUBLICATIONS

Lamansky, Sergey; Djurovich, Peter; Murphy, Drew; Abdel-Razzaq, Feras; Lee, Hae-Eun; Adachi, Chihaya; Burrows, Paul E.; Forrest, Stephen R.; and Thompson, Mark E.,"Highly Phosphorescent Bis-Cyclometalated Iridium Complexes: Synthesis, Photophysical Characterization, and Use in Organic Light Emitting Diodes"; J. Am. Chem. Soc. 2001, 123, pp. 4304-4312.
Lamansky, Sergey; Djurovich, Peter; Murphy, Drew; Abdel-Razzaq, Feras; Lee, Hae-Eun; Adachi, Chihaya; Burrows, Paul E.; Forrest, Stephen R.; and Thompson, Mark E., "Synthesis and Characterization of Phosphorescent Cyclometalated Iridium Complexes"; Inorg. Chem. 2001, 40, pp. 1704-1711.
Grushin, Vladimir V.; Herron, Norman; LeCloux, Daniel D.; Marshall, William J., Petrov, Viacheslav A.; "New, efficient electroluminescent materials based on organometallic Ir complexes," Chem. Commun., 2001, pp. 1494-1495.
PCT International Search Report dated Apr. 11, 2007; International Application No. PCT/KR2007/000112; International Filing Date Jan. 8, 2007. All references cited in the Search Report and not previously submitted are listed above.
PCT International Written Opinion dated Apr. 11, 2007; International Application No. PCT/KR2007/000112; International Filing Date Jan. 8, 2007. All references cited in the Opinion and not previously submitted are listed above.

* cited by examiner

*Primary Examiner* — Rebecca L Anderson
*Assistant Examiner* — Alicia L Otton
(74) *Attorney, Agent, or Firm* — Cantor Colburn LLP

(57) ABSTRACT

The present invention relates to a light emitting binuclear transition metal compound of Chemical Formulae 1 and 2, and an organic electroluminescence device including the compound. In the Chemical Formulae 1 and 2, M is selected from Ir, Pt, Rh, Re, and Os, and m is 2, provided that the m is 1 when M is Pt.

2 Claims, No Drawings

METALLIC COMPOUND AND ORGANIC ELECTROLUMINESCENCE DEVICE COMPRISING THE SAME

TECHNICAL FIELD

The present invention relates to a metallic compound and an organic electroluminescence device including the same, and more particularly, to a metallic compound that is applicable as a highly efficient phosphor host material and an organic electroluminescence device including the same.

BACKGROUND OF ART

An electroluminescence device (EL device) is a self-light emitting display device having such merits as a wide viewing angle and excellent contrast as well as a quick response time.

EL devices are classified into an inorganic EL device and an organic EL device in accordance with a material used for a light emitting layer. The organic EL device has merits of improved luminance, driving voltage, response speed, and multi-colorfying property compared to an inorganic EL device.

An organic EL device is generally composed of an anode on a substrate, a hole transport layer on the anode, and a light emitting layer, an electron transport layer (ETL), and a cathode sequentially positioned thereon. The hole transport layer, light emitting layer, and electron transport layer (ETL) are organic films that are composed of organic compounds.

The organic EL device having the above structure is operated as follows.

When a voltage is applied to a space between the anode and the cathode, the holes are injected from the anode to the light emitting layer through the hole transport layer. Meanwhile, when the electrons are injected from the cathode into the light emitting layer through the electron transport layer (ETL), carriers are recombined in the region of the light emitting layer to thereby produce excitons. The state of the excitons is changed from an exited state to a base state, and the change in the state of the excitons makes the molecules of the light emitting layer emit light to thereby form an image.

Materials for forming a light emitting layer are divided into fluorescent materials using singlet excitons and phosphorescent materials using triplet excitons according to the light emitting mechanism. Phosphorescent materials generally include organic/inorganic compound structures including transition element atoms. The transition element atoms change triplet excitons, which used to be impossible to transition, into excitons that are possible to transition, causing them to emit phosphorescent light. Since the phosphorescent materials can use triplet excitons having a generation probability of 75%, higher luminous efficiency can be achieved than with fluorescent materials using singlet excitons having a generation probability of 25%.

Among light emitting materials using the triplet excitons are phosphorescent materials including iridium and platinum compounds (Sergey Lamansky et al. Inorg. Chem., 40, 1704-1711, 2001, and Sergey Lamansky et al., J. Am. Chem. Soc., 123, 4304-4312, 2001). For blue light emitting materials, Ir compounds based on $(4,6-F_2ppy)_2Irpic$ or a fluorinated ppy ligand structure have been developed (Vladimir V. Grushin et al., Chem. Commun., 1494-1495, 2001). The $(4,6-F_2ppy)_2Irpic$, however, has shortcomings that it emits light in a sky blue region and its large shoulder peaks increase a y value in color purity coordinates. Researchers are studying red and green light emitting materials, but there still remains great demand to develop highly efficient phosphorescent materials having a long lifespan.

DETAILED DESCRIPTION OF THE INVENTION

Technical Problem

In order to solve the problems, the object of the present invention is to provide a phosphor dimeric metallic compound having a new co-ligand structure and an organic electroluminescence device having improved luminous efficiency and color purity.

Technical Solution

The present invention relates to a light-emitting binuclear transition metal compound represented by the following Chemical Formula 1 and Chemical Formula 2, and an organic electroluminescence device including the same:

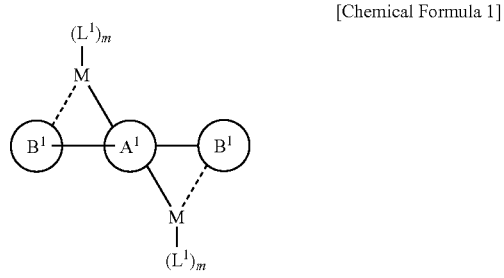

[Chemical Formula 1]

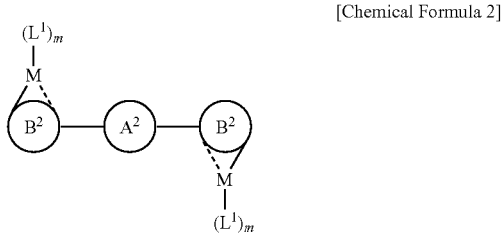

[Chemical Formula 2]

Wherein, in the above Chemical Formulae 1 and 2, M is Ir, Pt, Rh, Re, Os, and the like, m is 2, provided that the m is 1 when M is Pt, $A^1$ and $B^1$ in the above Formula 1 are represented by the following Formula 3:

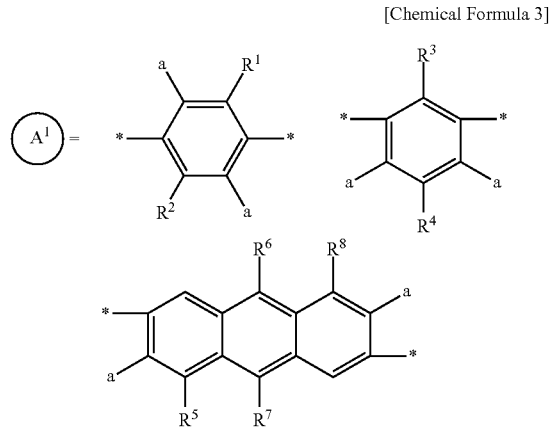

[Chemical Formula 3]

-continued

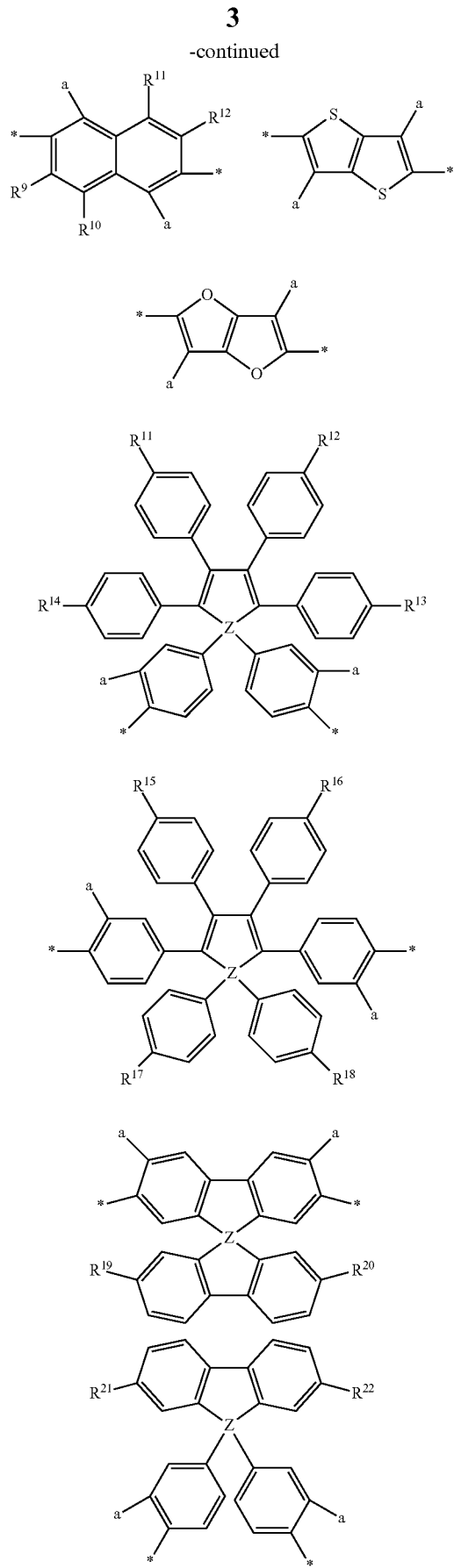

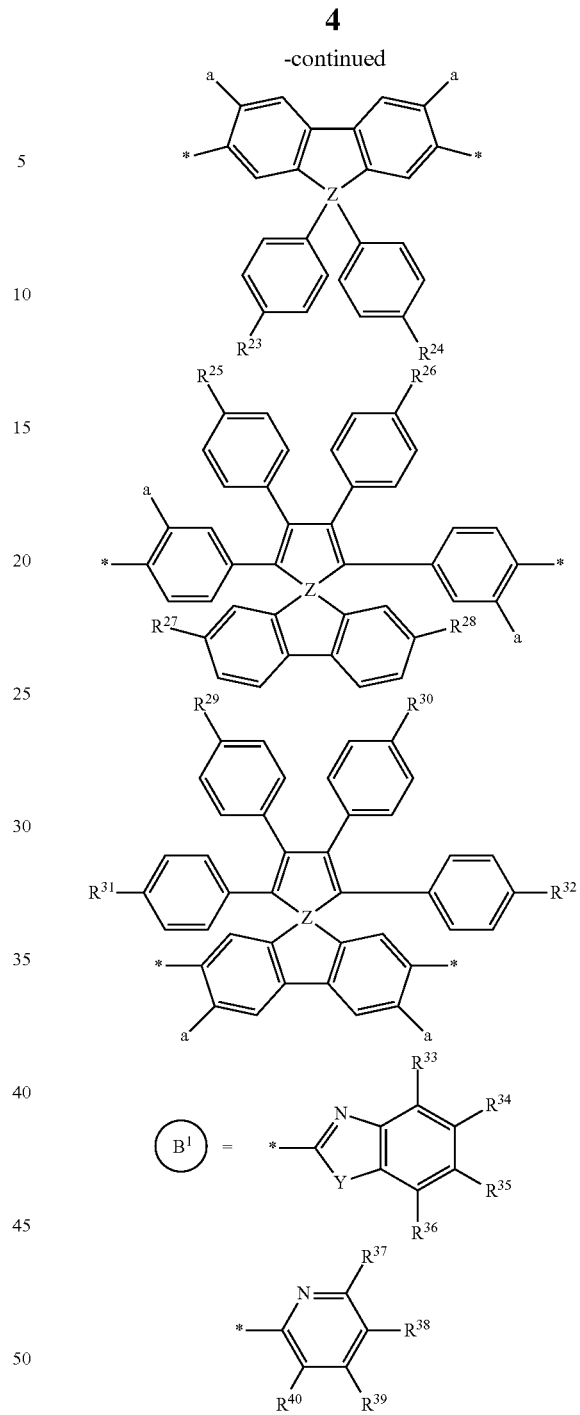

Wherein, in the above Formula 3, $A^1$ is bound with a portion denoted as * and adjacent $B^1$ by a covalent bond, and the transition metal, M forms a complex compound by a covalent with a portion denoted as "a" of $A^1$ and by a coordination bond with a N atom of $B^1$, Z is a Si, or C atom, $R^1$-$R^{32}$, $R^{34}$, $R^{35}$, $R^{36}$, $R^{38}$, $R^{39}$, and $R^{40}$ are the same or different, and are selected from hydrogen, a C1 to C20 alkyl, an aryl, a cycloalkyl, a halogen, a linear or branched substituent including at least one halogen, a linear or branched substituent including at least one heteroatom, carbonyl, vinyl, and acetylenyl, or form a cycle, and $R^{33}$, and $R^{37}$ are hydrogen, a C1 to C20 alkyl excluding an aromatic cyclic substituent, a cycloalkyl, a halogen, a linear or branched substituent including at least one halogen, or a linear or branched substituent including at least one heteroatom.
In the above Chemical Formula 2, $A^2$, and $B^2$ are represented by the following Chemical Formula 4:
[Chemical Formula 4]
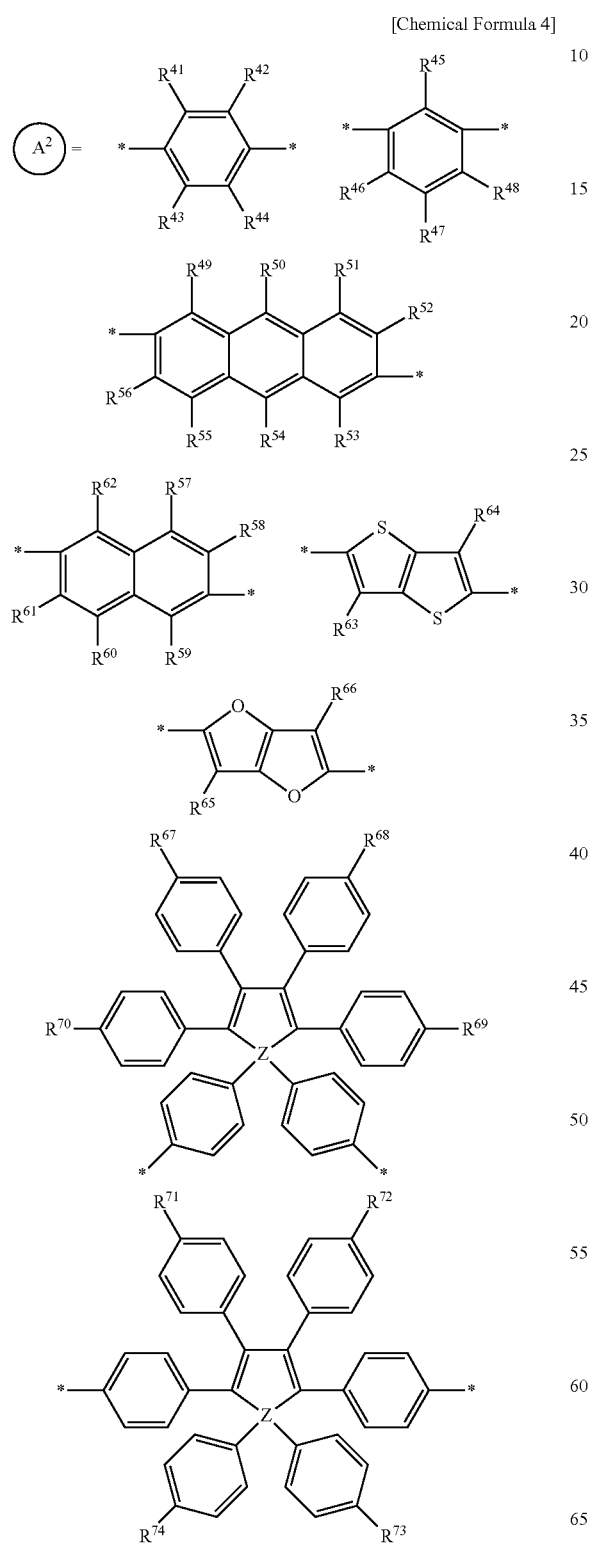
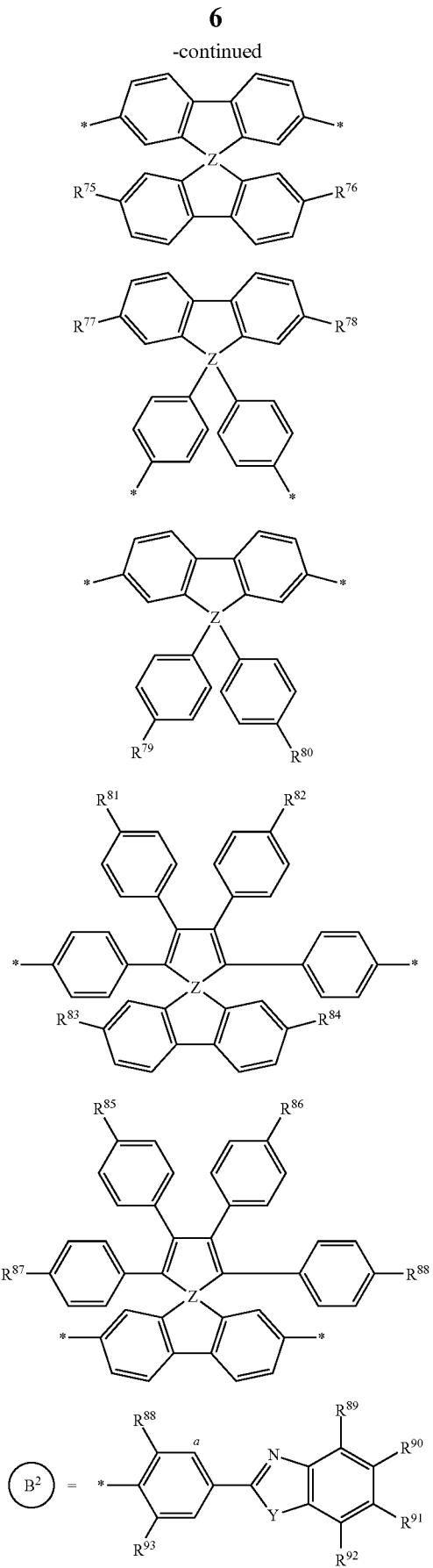

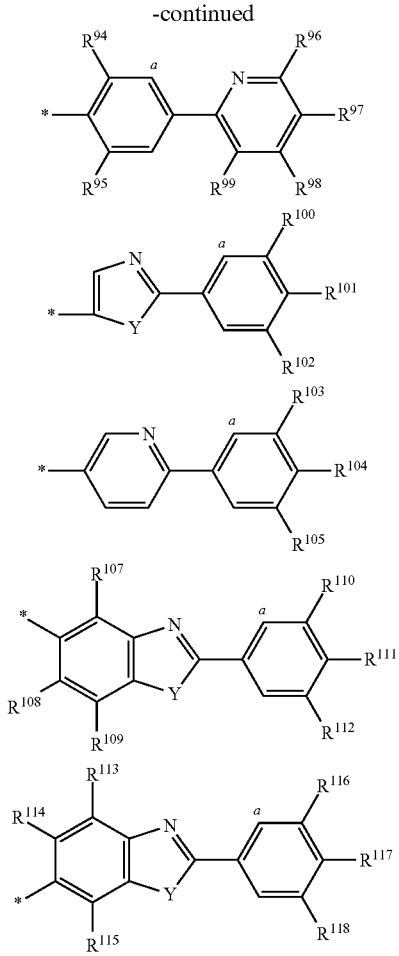

In the above Formula 4, $A^2$ is bound with a portion denoted as * and $B^2$ by a covalent bond, and the transition metal, M forms a complex compound by a covalent with a portion denoted as "a" of $B^2$ and by a coordination bond with a N atom of $B^2$, Z is a Si, or C atom, $R^{41}$-$R^{88}$, $R^{90}$-$R^{95}$, $R^{97}$-$R^{106}$, $R^{108}$-$R^{112}$, and $R^{114}$-$R^{118}$ are the same or different, and are selected from hydrogen, a C1 to C20 alkyl, an aryl, a cycloalkyl, a halogen, a linear or branched substituent including at least one halogen, a linear or branched substituent including at least one heteroatom, carbonyl, vinyl, and acetylenyl, or form a cycle, and $R^{89}$, $R^{96}$, $R^{107}$, and $R^{113}$ are hydrogen, a C1 to C20 alkyl excluding an aromatic cyclic substituent, a cycloalkyl, a halogen, a linear or branched substituent including at least one halogen, or a linear or branched substituent including at least one heteroatom.

In the above Chemical Formulae 1 and 2, $L^1$ is represented by the following Chemical Formula 5:

[Chemical Formula 5]

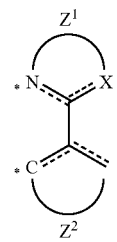

$L^1$ in the above Formula 5, is a independent ligand having a covalent bond site with a carbon denoted as * and a coordination bond with nitrogen and forming a complex compound with the transition metal M, and X is a hetero atom of nitrogen, oxygen, sulfur, phosphorus, and so on, and $Z^1$ and $Z^2$ are atoms for forming a C4 to C7 aromatic hydrocarbon ring or aromatic heterocyclic ring.

The transition metal compound includes a symmetric aromatic derivative, and a fluorene or thiol-based derivative a co-ligand having two C—N chelating binding sites.

The examples of the co-ligand are represented by the following Chemical Formulae 6:

[Chemical Formulae 6]

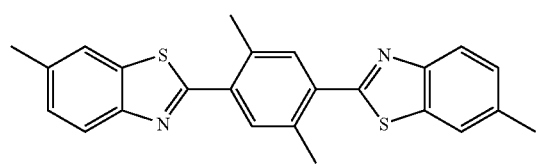 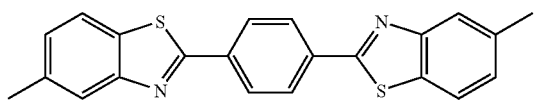

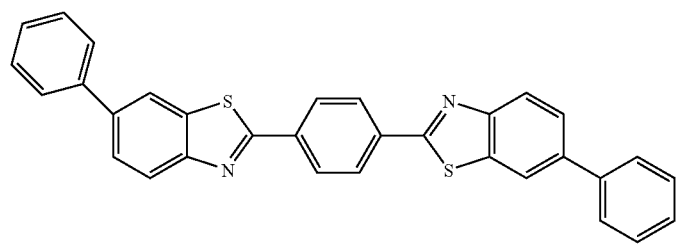

-continued
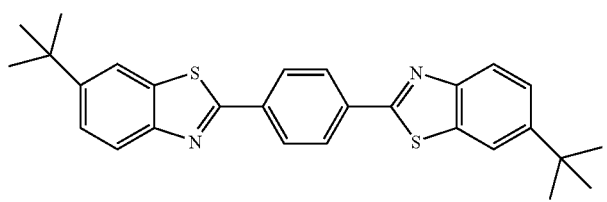
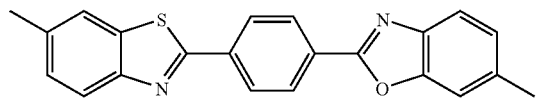
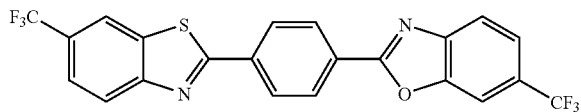
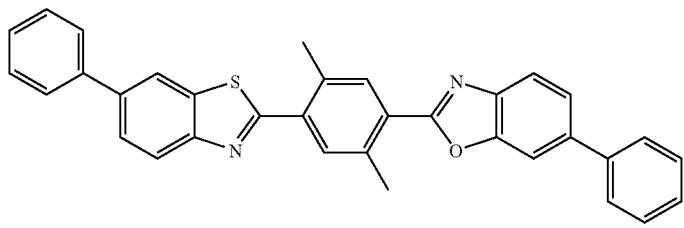
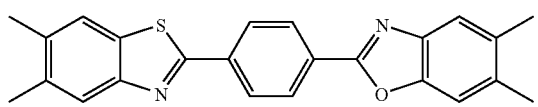
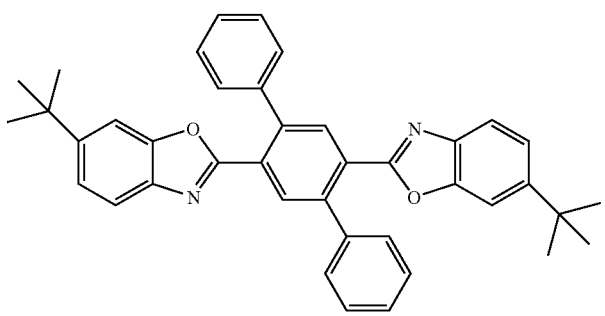
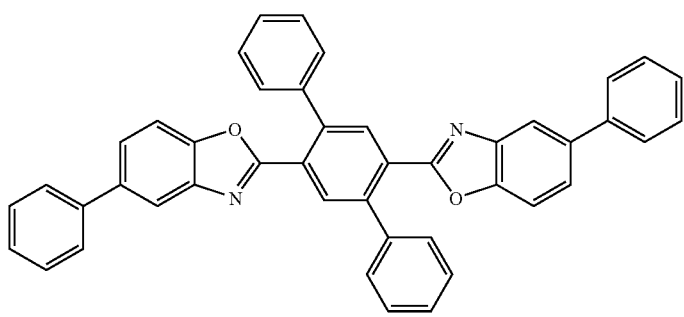
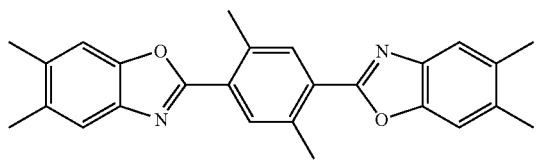
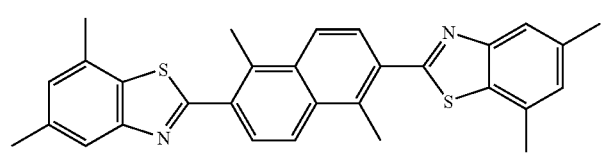
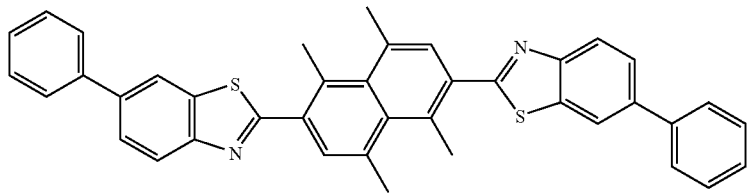

-continued
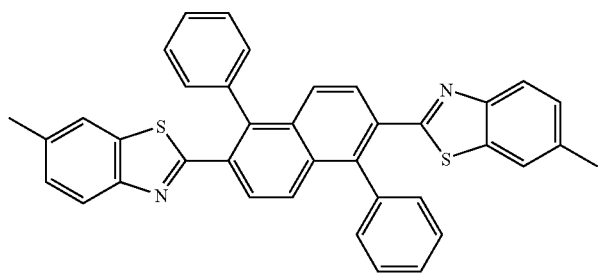
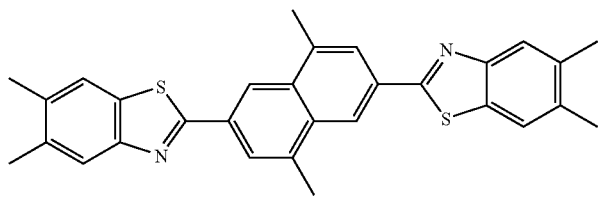
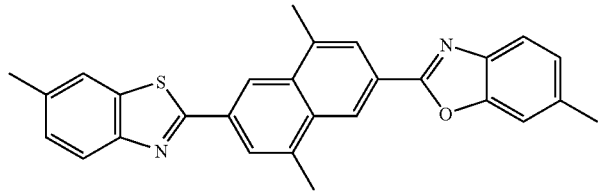
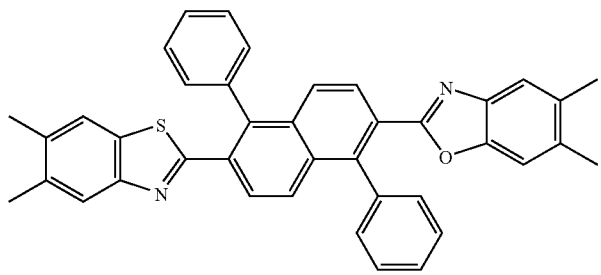
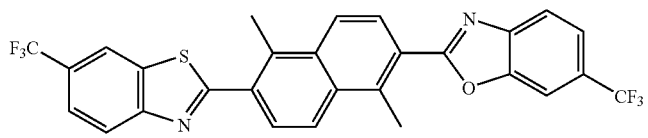
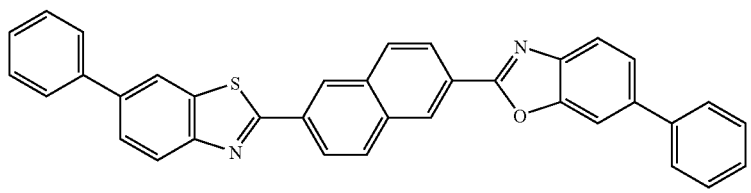
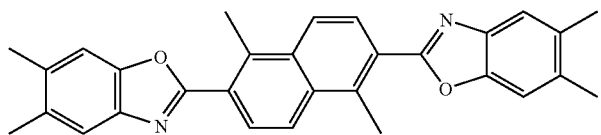
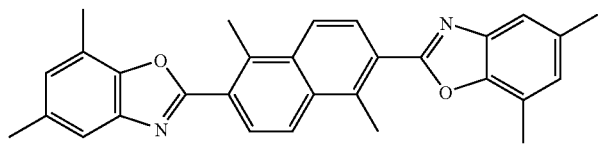

-continued
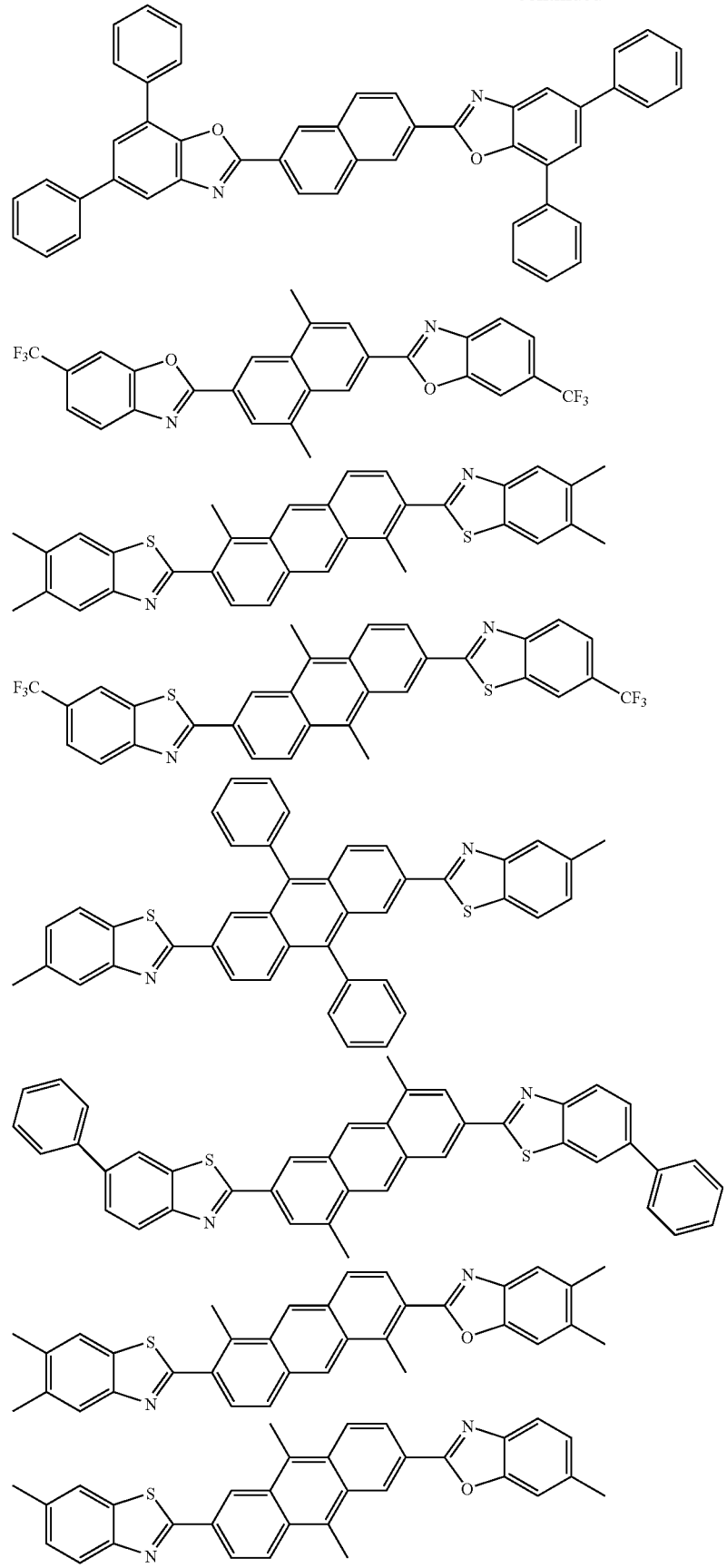

-continued
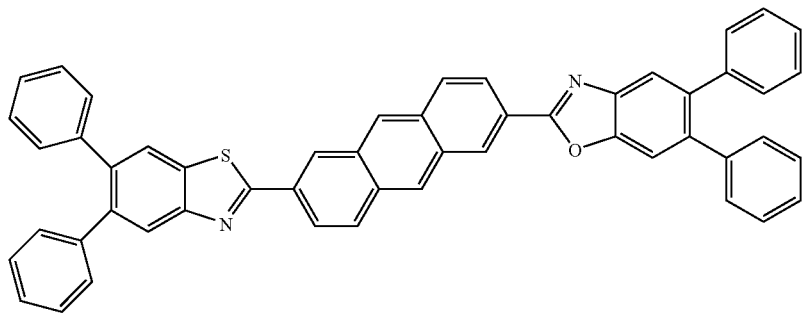
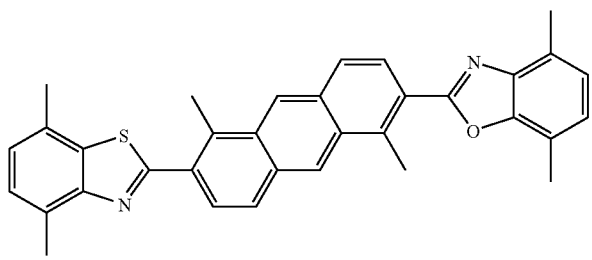
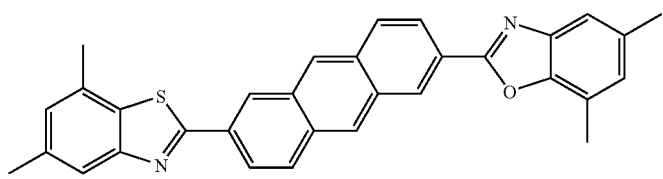
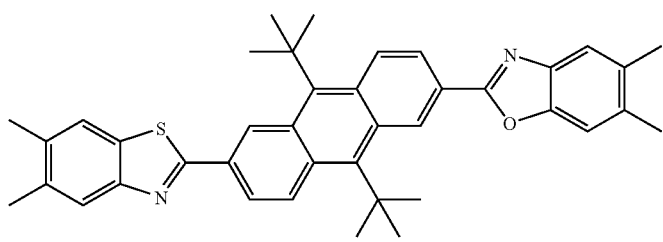
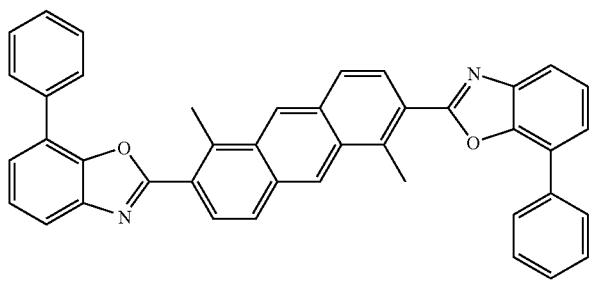
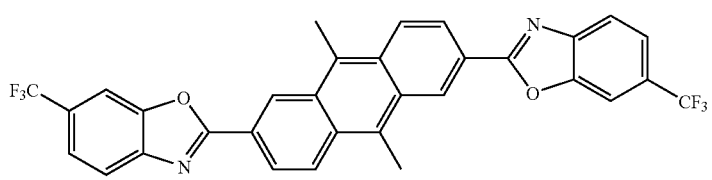
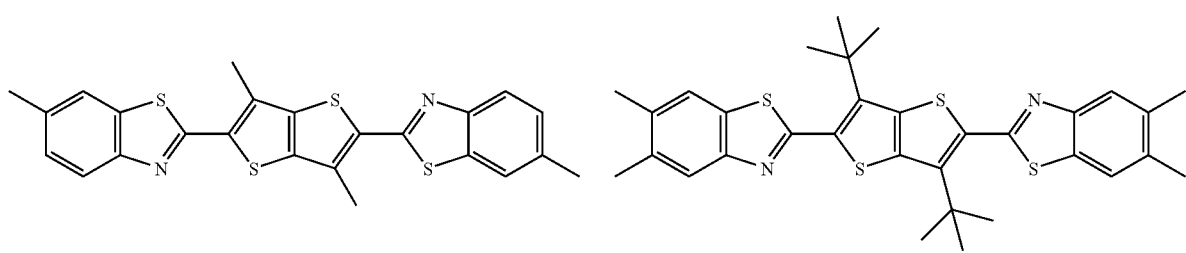

-continued
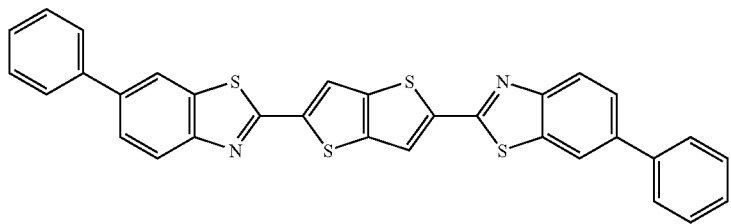
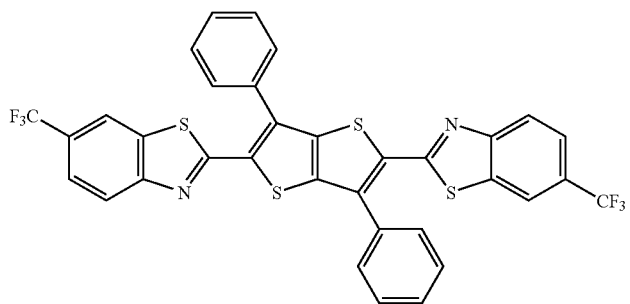
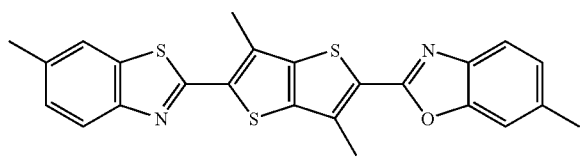
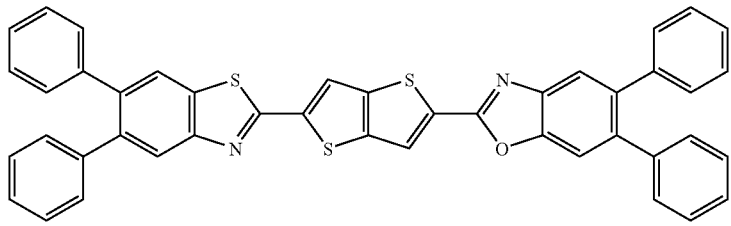
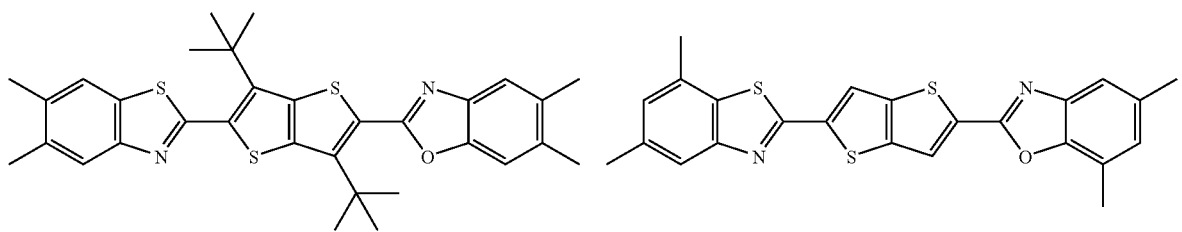
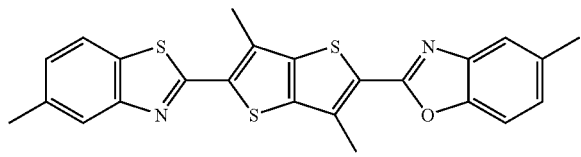
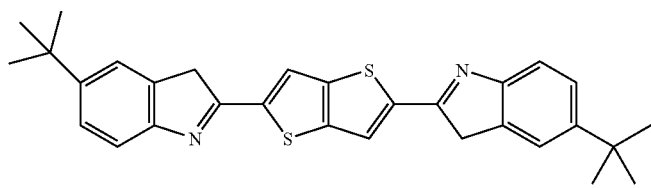

-continued
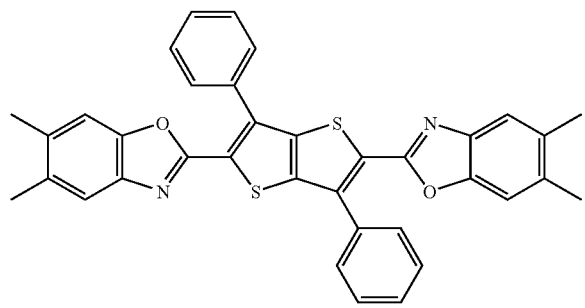
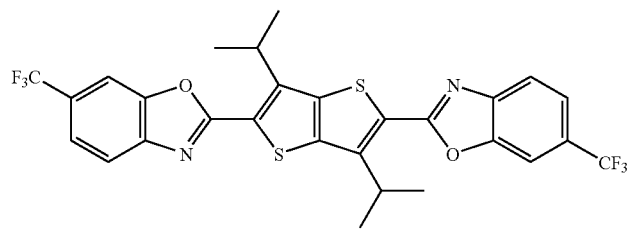
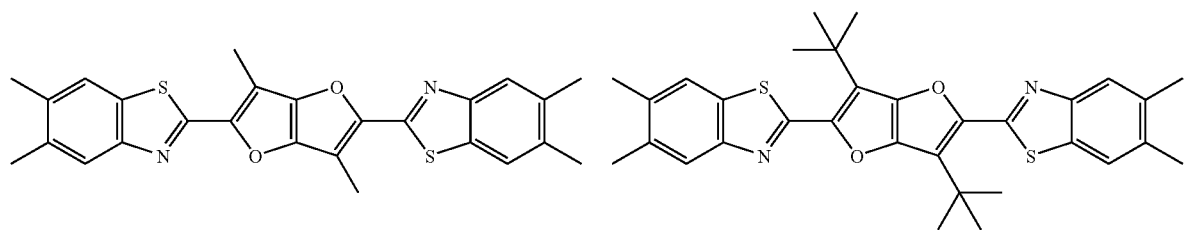
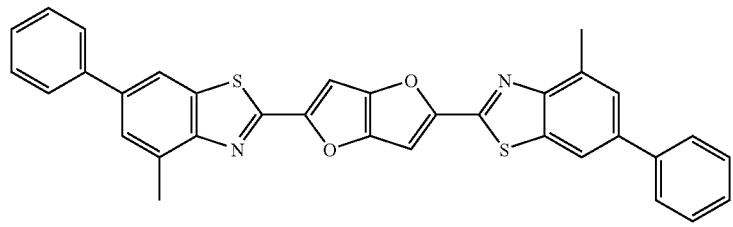
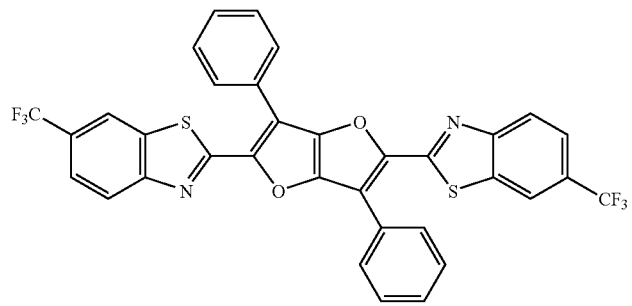
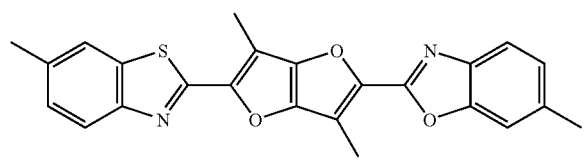
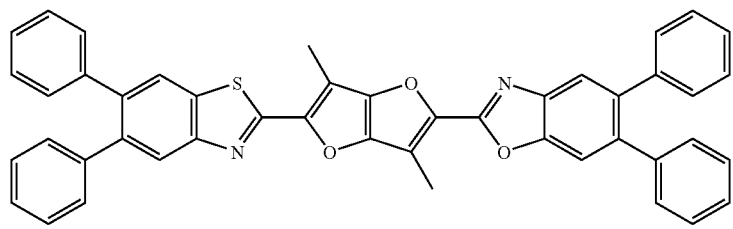

-continued
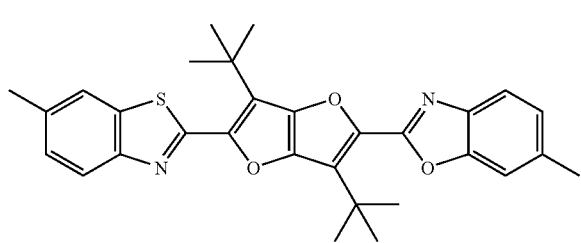
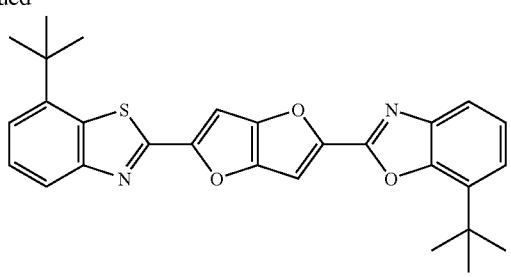
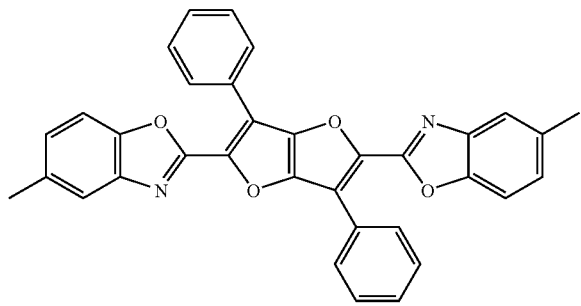
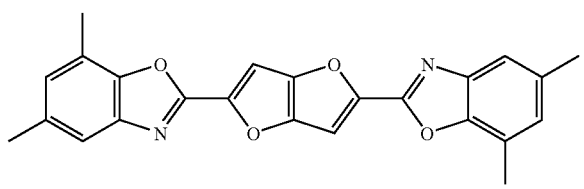
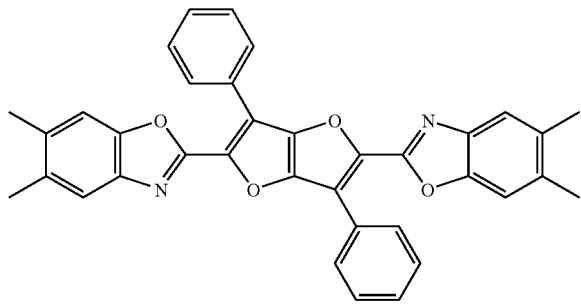
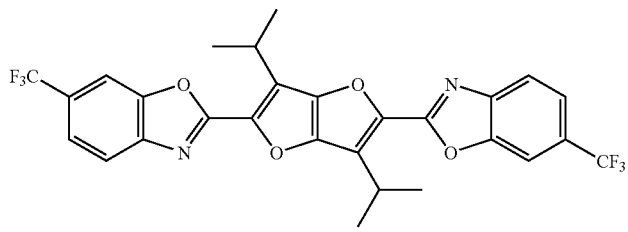
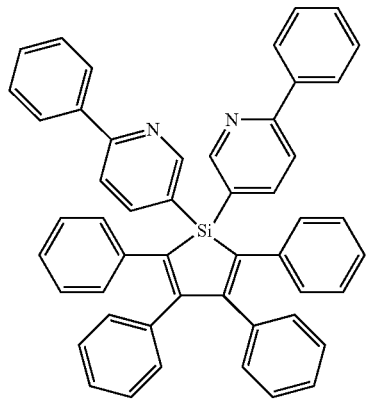
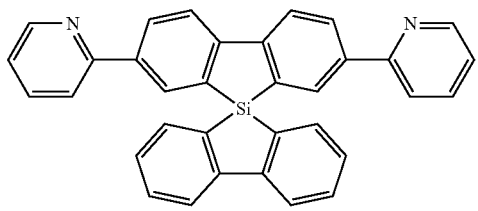
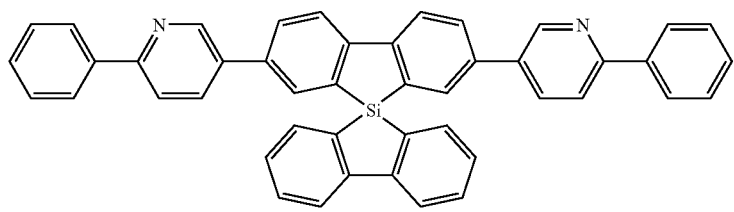

-continued

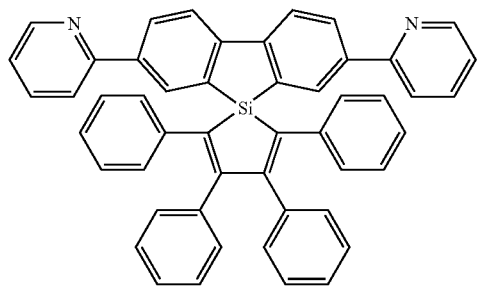

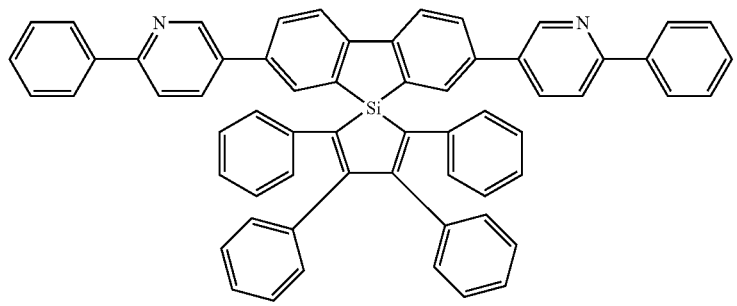

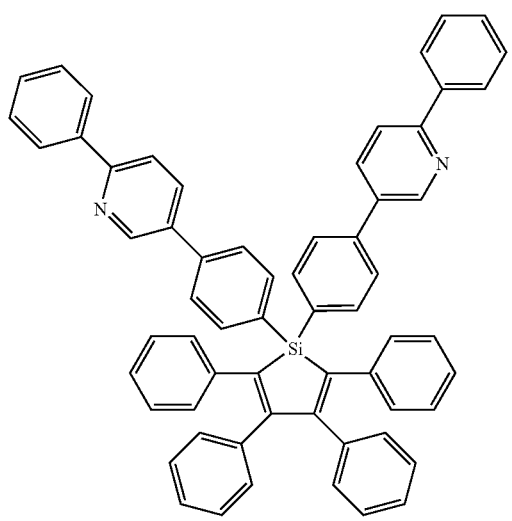

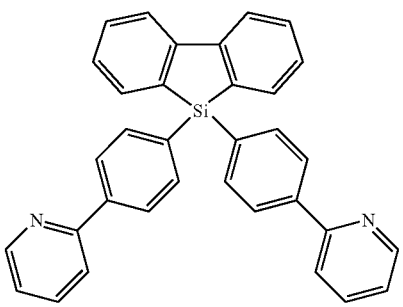

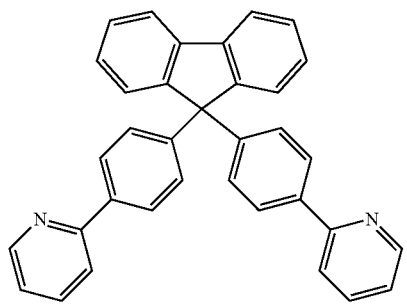

A functional group having a large steric hindrance such as an alkyl, an aryl, a halogen, silyl, and so on can be independently introduced to each $L^1$ ligand. Several nm of light-emission and light wavelength can be easily controlled in accordance with the positions of the substituents and the properties of electron donors.

The $L^1$ ligands of the present invention are represented by the following Chemical Formulae 7:

[Chemical Formulae 7]

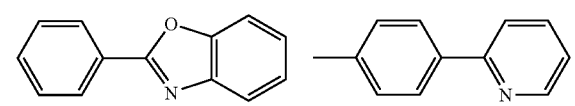

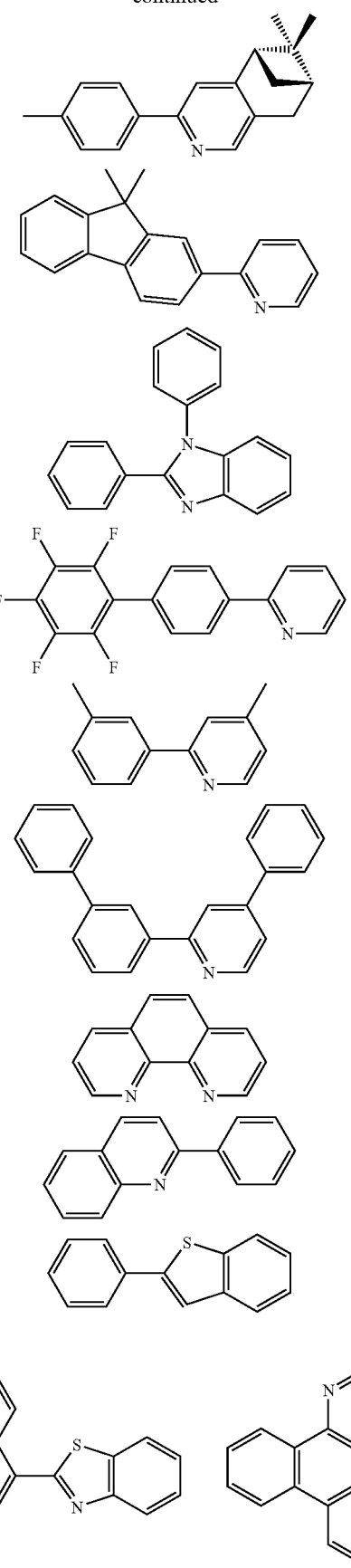
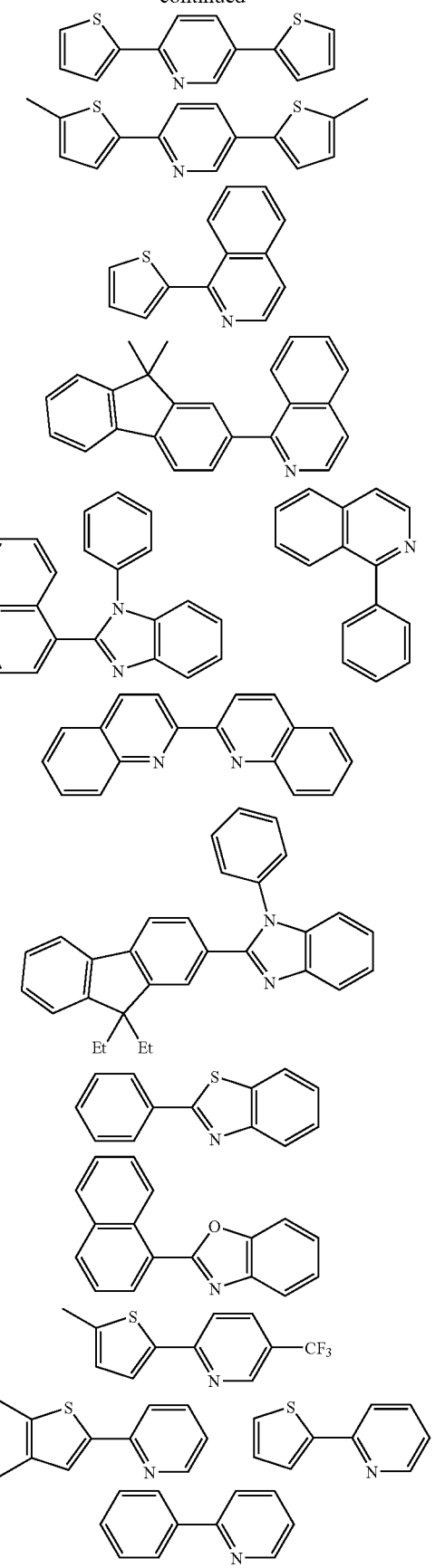

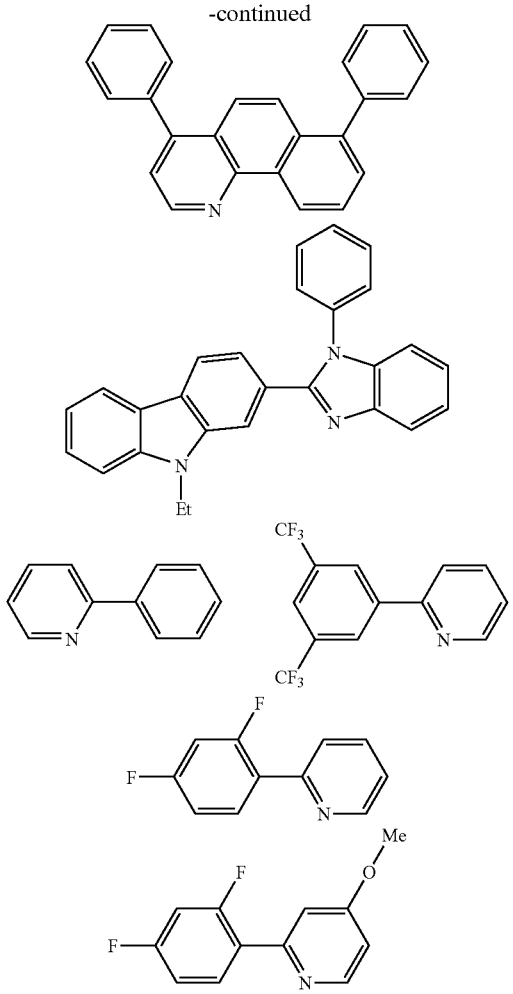
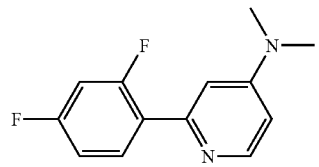
The transition metal compound represented by the above Chemical Formulae can be synthesized as follows. The following Reaction Schemes 1 and 2 show ligand syntheses, and Reaction Scheme 3 shows a metalation process.
[Rreaction Scheme 1]
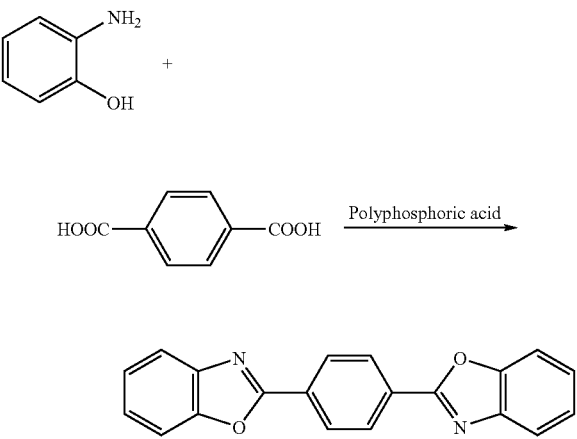
[Reaction Scheme 2]
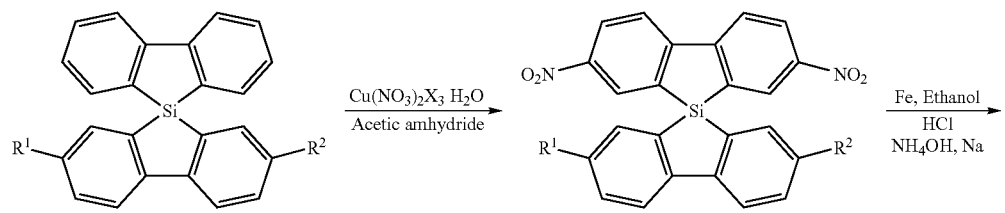
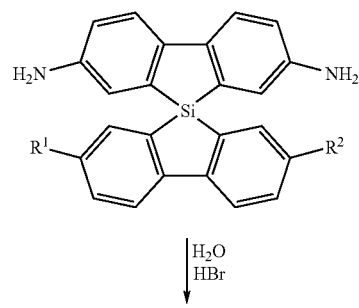

-continued

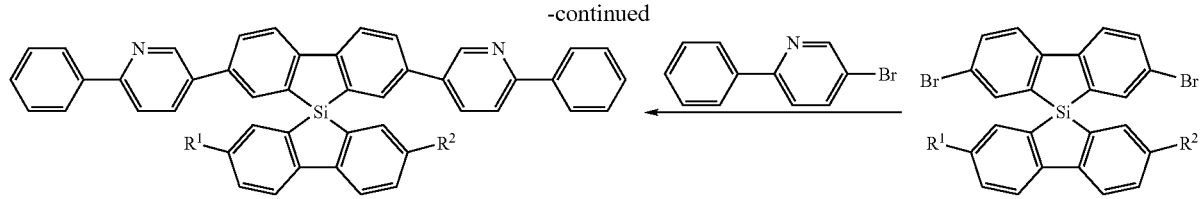

[Reaction Scheme 3]

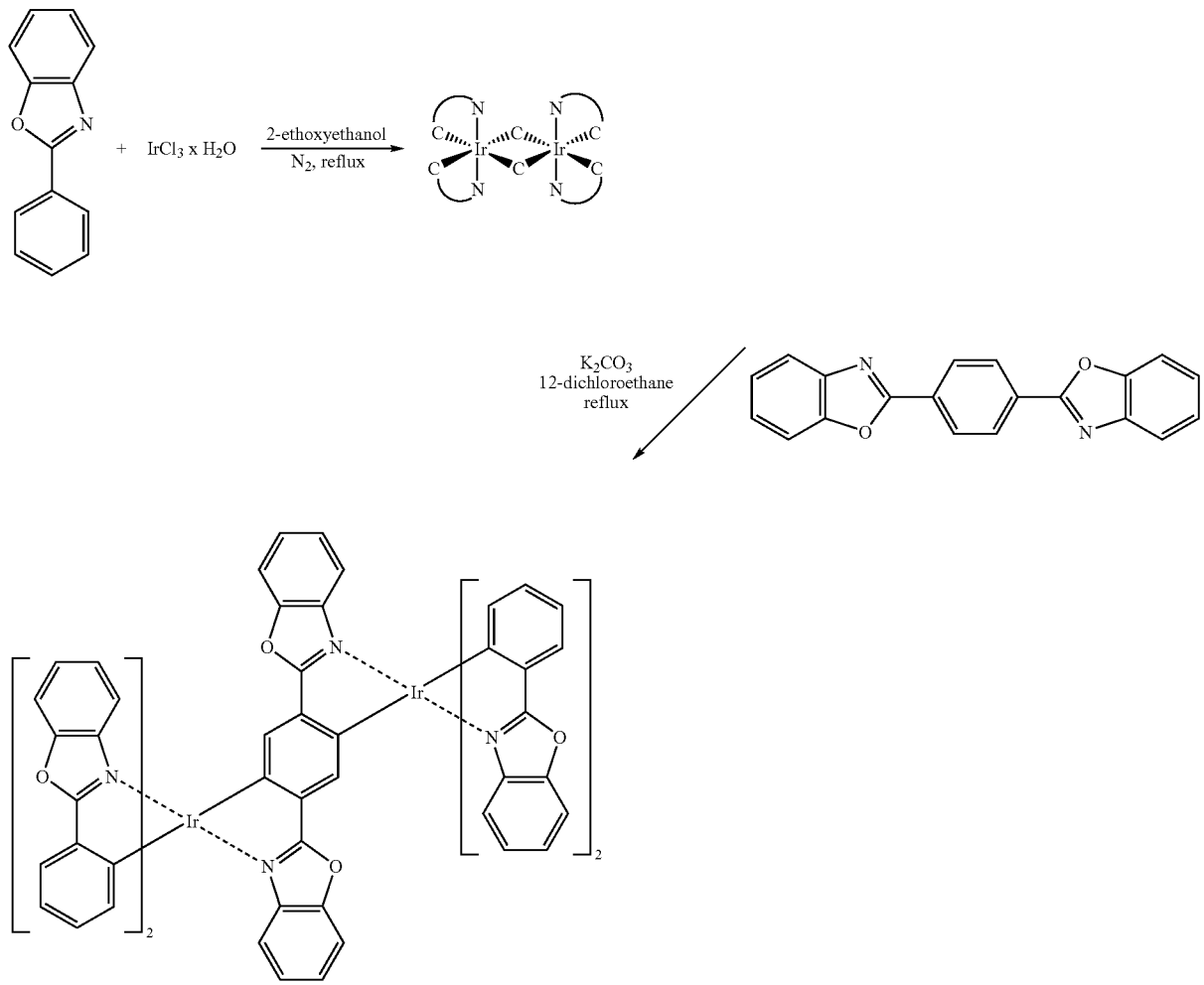

As shown in Reaction Scheme 3, a main ligand having C—N chelating site and hydrated iridium trichloride are reacted under a nitrogen atmosphere to prepare a dimmer intermediate that includes two iridium metals sharing a Cl ligand, and then the intermediate is reacted with a co-ligand in a solvent including a weak base to prepare the transition metal compound of Chemical Formula 1.

BEST MODE

The present invention can be specified by the following Examples. The Examples only illustrate the present invention and they do not limit the scope and range of the present invention, which is defined by the accompanying claims.

Example 1

Compound 1

Synthesis of (PBOZ)$_2$IR(BOZPBOZ)Ir(PBOZ)$_2$

Synthesis of 2-(4-(benzo[d]oxazole-2-yl)phenyl)benzo[d] oxazole (BOZPBOZ)s: diphosphoric acid (125 cm$^3$) was heated at 70° C. for 1 hour while agitating. 0.1 mol of terephthalic acid was added and the resulting mixture was stirred for 15 minutes. 0.2 mol of 2-aminophenol was added in a dropwise fashion for 10 minutes. The temperature of the mixture was increased to 150° C. and then this temperature was maintained for 2 hours. The mixture was stirred to cool down to a room temperature. The resulting reaction mixture was stirred for 1 hour with ice water (1.5 dm$^3$), and neutralized with a diluted sodium carbonate hydrate solution. Then it was filtered and dried in an oven for 1 day. The solid was crystallized from dimethylformamide (200 cm$^3$). The final filtered product was rinsed with methanol (100 cm$^3$) and then dried in a 100° C. vacuum oven. As a result, colorless needle-shaped crystalline 2-(4-(benzo[d]oxazole-2-yl)phenyl)benzo[d]oxazole was produced at a yield of 78%.

Synthesis of (PBOZ)$_2$Ir(Cl)$_2$Ir(PBOZ)$_2$: 5 mmol of 2-phenylbenzo[d]oxazole (PBOZ) and 10 mmol of IrCl$_3$×H$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce (PBOZ)$_2$Ir(Cl)$_2$Ir(PBOZ)$_2$ at a yield of 92%.

Synthesis of (PBOZ)$_2$Ir(BOZPBOZ)Ir(PBOZ)$_2$: 5 mmol of (PBOZ)$_2$Ir(Cl)$_2$Ir(PBOZ)$_2$, 25 mmol of 2-(4-(benzo[d]oxazole-2-yl)phenyl)benzo[d]oxazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce (PBOZ)$_2$Ir(BOZPBOZ)Ir(PBOZ)$_2$ at a yield of 91%.

Example 2

Compound 2

Synthesis of (F$_2$ppy)$_2$Ir(BOZPBOZ)Ir(F$_2$ppy)$_2$

Synthesis of (F$_2$ppy)$_2$Ir(Cl)$_2$Ir(F$_2$ppy)$_2$: 5 mmol of 3,5-difluoro-2-phenylpyridine(F$_2$ppy) and 10 mmol of IrCl$_3$×H$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce (F$_2$ppy)$_2$Ir(Cl)$_2$Ir(F$_2$ppy)$_2$ at a yield of 92%.

Synthesis of (F$_2$ppy)$_2$Ir(BOZPBOZ)Ir(F$_2$ppy)$_2$: 5 mmol of (F$_2$ppy)$_2$Ir(Cl)$_2$Ir(F$_2$ppy)$_2$, 25 mmol of 2-(4-(benzo[d]oxazole-2-yl)phenyl)benzo[d]oxazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce (F$_2$ppy)$_2$Ir(BOZPBOZ)Ir(F$_2$ppy)$_2$ at a yield of 87%.

Example 3

Compound 3

Synthesis of (PBTZ)$_2$Ir(BOZPBOZ)Ir(PBTZ)$_2$

Synthesis of (PBTZ)$_2$Ir(Cl)$_2$Ir(PBTZ)$_2$: 5 mmol of 2-phenylbenzo[d]oxazole (PBTZ) and 10 mmol of IrCl$_3$×H$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce (PBTZ)$_2$Ir(Cl)$_2$Ir(PBTZ)$_2$ at a yield of 92%.

Synthesis of (PBTZ)$_2$Ir(BOZPBOZ)Ir(PBTZ)$_2$: 5 mmol of (PBTZ)$_2$Ir(Cl)$_2$Ir(PBTZ)$_2$, 25 mmol of 2-(4-(benzo[d]oxazole-2-yl)phenyl)benzo[d]oxazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce (PBTZ)$_2$Ir(BOZPBOZ)Ir(PBTZ)$_2$ at a yield of 86%.

Example 4

Compound 4

Synthesis of (PTPD)$_2$Ir(BOZPBOZ)Ir(PTPD)$_2$

Synthesis of (PTPD)$_2$Ir(Cl)$_2$Ir(PTPD)$_2$: 5 mmol of 2-p-tolylpyridine (PTPD) and 10 mmol of IrCl$_3$×H$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce (PTPD)$_2$Ir(Cl)$_2$Ir(PTPD)$_2$ at a yield of 92%.

Synthesis of (PTPD)$_2$Ir(BOZPBOZ)Ir(PTPD)$_2$: 5 mmol of (PTPD)$_2$Ir(Cl)$_2$Ir(PTPD)$_2$, 25 mmol of 2-(4-(benzo[d]oxazole-2-yl)phenyl)benzo[d]oxazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce (PTPD)$_2$Ir(BOZPBOZ)Ir(PTPD)$_2$ at a yield of 88%.

Example 5

Compound 5

Synthesis of (DMFIQ)$_2$Ir(BOZPBOZ)Ir(DMFIQ)$_2$

Synthesis of (DMFIQ)$_2$Ir(Cl)$_2$Ir(DMFIQ)$_2$: 5 mmol of 1-(9,9-dimethyl-9H-fluoren-7-yl)isoquinoline (DMFIQ) and 10 mmol of IrCl$_3$×H$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce (DMFIQ)$_2$Ir(Cl)$_2$Ir(DMFIQ)$_2$ at a yield of 92%.

Synthesis of (DMFIQ)$_2$Ir(BOZPBOZ)Ir(DMFIQ)$_2$: 5 mmol of (DMFIQ)$_2$Ir(Cl)$_2$Ir(DMFIQ)$_2$, 25 mmol of 2-(4-(benzo[d]oxazole-2-yl)phenyl)benzo[d]oxazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce (DMFIQ)$_2$Ir(BOZPBOZ)Ir(DMFIQ)$_2$ at a yield of 85%.

Example 6

Synthesis of Compound (PBOZ)$_2$Ir(BTZPBTZ)Ir(PBOZ)$_2$

Synthesis of 2-(4-(benzo[d]thiazole-2-yl)phenyl)benzo[d]thiazole (BTZPBTZ): polyphosphoric acid (125 cm$^3$) was heated at 70° C. for 1 hour while agitating. 0.1 mol of terephthalic acid was added and the resulting mixture was stirred for 15 minutes. 0.2 mol of 2-aminobenzenethiazole was added in a dropwise fashion for 10 minutes. The temperature of the mixture was increased to 150° C. and then this temperature was maintained for 2 hours. The mixture was stirred to cool down to a room temperature. The resulting reaction mixture was stirred for 1 hour with ice water (1.5 dm3), and neutralized with a diluted sodium carbonate hydrate solution. Then it was filtered and dried in an oven for 1 day. The solid was crystallized from dimethylformamide (200 cm$^3$). The final filtered product was rinsed with methanol (100 cm$^3$) and then dried in a 100° C. vacuum oven. As a result, colorless needle-shaped crystalline 2-(4-(benzo[d]thiazole-2-yl)phenyl)benzo[d]thiazole was produced at a yield of 78%.

Synthesis of $(PBOZ)_2Ir(Cl)_2Ir(PBOZ)_2$: 5 mmol of 2-phenylbenzo[d]oxazole (PBOZ) and 10 mmol of $IrCl_3 \times H_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce $(PBOZ)_2Ir(Cl)_2Ir(PBOZ)_2$ at a yield of 92%.

Synthesis of $(PBOZ)_2Ir(BTZPBTZ)Ir(PBOZ)_2$: 5 mmol of $(PBOZ)_2Ir(Cl)_2Ir(PBOZ)_2$ and 25 mmol of 2-(4-(benzo[d]thiazole-2-yl)phenyl)benzo[d]thiazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce $(PBOZ)_2Ir(BTZPBTZ)Ir(PBOZ)_2$ at a yield of 90%.

Example 7

Compound 7

Synthesis of $(F_2ppy)_2Ir(BTZPBTZ)Ir(F_2ppy)_2$

Synthesis of $(F_2ppy)_2Ir(Cl)_2Ir(F_2ppy)_2$: 5 mmol of 3,5-difluoro-2-phenylpyridine($F_2ppy$)pyridine and 10 mmol of $IrCl_3 \times H_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce $(F_2ppy)_2Ir(Cl)_2Ir(F_2ppy)_2$ at a yield of 92%.

Synthesis of $(F_2ppy)_2Ir(BTZPBTZ)Ir(F_2ppy)_2$: 5 mmol of $(F_2ppy)_2Ir(Cl)_2Ir(F_2ppy)_2$, 25 mmol of 2-(4-(benzo[d]thiazole-2-yl)phenyl)benzo[d]thiazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce $(F_2ppy)_2Ir(BTZPBTZ)Ir(F_2ppy)_2$ at a yield of 86%.

Example 8

Compound 3

Synthesis of $(PBTZ)_2Ir(BTZPBTZ)Ir(PBTZ)_2$

Synthesis of $(PBTZ)_2Ir(Cl)_2Ir(PBTZ)_2$: 5 mmol of 2-phenylbenzo[d]thiazole (PBTZ) and 10 mmol of $IrCl_3 \times H_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce $(PBTZ)_2Ir(Cl)_2Ir(PBTZ)_2$ at a yield of 92%.

Synthesis of $(PBTZ)_2Ir(BTZPBTZ)Ir(PBTZ)_2$: 5 mmol of $(PBTZ)_2Ir(Cl)_2Ir(PBTZ)_2$, 25 mmol of 2-(4-(benzo[d]thiazole-2-yl)phenyl)benzo[d]thiazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce $(PBTZ)_2Ir(BTZPBTZ)Ir(PBTZ)_2$ at a yield of 87%.

Example 9

Compound 9

Synthesis of $(PTPD)_2Ir(BTZPBTZ)Ir(PTPD)_2$

Synthesis of $(PTPD)_2Ir(Cl)_2Ir(PTPD)_2$: 5 mmol of 2-p-tolylpyridine (PTPD) and 10 mmol of $IrCl_3 \times H_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce $(PTPD)_2Ir(Cl)_2Ir(PTPD)_2$ at a yield of 92%.

Synthesis of $(PTPD)_2Ir(BTZPBTZ)Ir(PTPD)_2$: 5 mmol of $(PTPD)_2Ir(Cl)_2Ir(PTPD)_2$, 25 mmol of 2-(4-(benzo[d]thiazole-2-yl)phenyl)benzo[d]thiazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce $(PTPD)_2Ir(BTZPBTZ)Ir(PTPD)_2$ at a yield of 84%.

Example 10

Compound 10

Synthesis of $(DMFIQ)_2Ir(BTZPBTZ)Ir(DMFIQ)_2$

Synthesis of $(DMFIQ)_2Ir(Cl)_2Ir(DMFIQ)_2$: 5 mmol of 1-(9,9-dimethyl-9H-fluoren-7-yl)isoquinoline (DMFIQ) and 10 mmol of $IrCl_3 \times H_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce $(DMFIQ)_2Ir(Cl)_2Ir(DMFIQ)_2$ at a yield of 92%.

Synthesis of $(DMFIQ)_2Ir(BTPBTZ)Ir(DMFIQ)_2$: 5 mmol of $(DMFIQ)_2Ir(Cl)_2Ir(DMFIQ)_2$, 25 mmol of 2-(4-(benzo[d]thiazole-2-yl)phenyl)benzo[d]thiazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce $(DMFIQ)_2Ir(BTZPBTZ)Ir(DMFIQ)_2$ at a yield of 87%.

Example 11

Synthesis of Compound (PBOZ)$_2$Ir(BOZNBOZ)Ir(PBOZ)$_2$

Synthesis of 2-(2-(benzo[d]oxazole-2-yl)naphthalene-6-yl)benzo[d]oxazole polyphosphoric acid (125 cm$^3$) was heated at 70° C. for 1 hour while agitating. 0.1 mol of naphthalene-2,6-dicarboxylic acid was added and the resulting mixture was stirred for 15 minutes. 0.2 mol of 2-aminophenol was added in a dropwise fashion for 10 minutes. The temperature of the mixture was increased to 150° C. and then this temperature was maintained for 2 hours. The mixture was stirred to cool down to a room temperature. The resulting reaction mixture was stirred for 1 hour with ice water (1.5 dm3), and neutralized with a diluted sodium carbonate hydrate solution. Then it was filtered and dried in an oven for 1 day. The solid was crystallized from dimethylformamide (200 cm$^3$). The final filtered product was rinsed with methanol (100 cm$^3$) and then dried in a 100° C. vacuum oven. As a result, colorless needle-shaped crystalline 2-(2-(benzo[d]oxazole-2-yl)naphthalene-6-yl) benzo[d]oxazole was produced at a yield of 75%.

Synthesis of (PBOZ)$_2$Ir(Cl)$_2$Ir(PBOZ)$_2$: 5 mmol of PBOZ and 10 mmol of IrCl$_3$×H$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce (PBOZ)$_2$Ir(Cl)$_2$Ir(PBOZ)$_2$ at a yield of 92%.

Synthesis of (PBOZ)$_2$Ir(BOZNBOZ)Ir(PBOZ)$_2$: 5 mmol of (PBOZ)$_2$Ir(Cl)$_2$IrPBOZ)$_2$, 25 mmol of 2-(2-(benzo[d]oxazole-2-yl)naphthalene-6-yl)benzo[d]oxazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce (PBOZ)$_2$Ir(BOZNBOZ)Ir(PBOZ)$_2$ at a yield of 90%.

Example 12

Synthesis of Compound (PBTZ)$_2$Ir(BOZNBOZ)Ir(PBTZ)$_2$

Synthesis of (PBOZ)$_2$Ir(Cl)$_2$Ir(PBOZ)$_2$: 5 mmol of PBOZ and 10 mmol of IrCl$_3$×H$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce (PBOZ)$_2$Ir(Cl)$_2$Ir(PBOZ)$_2$ at a yield of 90%.

Synthesis of (PBTZ)$_2$Ir(BOZNBOZ)Ir(PBTZ)$_2$: 5 mmol of (PBOZ)$_2$Ir(Cl)$_2$IrPBOZ)$_2$, 25 mmol of 2-(2-(benzo[d]oxazole-2-yl)naphthalene-6-yl)benzo[d]thiazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce (PBTZ)$_2$Ir(BOZNBOZ)Ir(PBTZ)$_2$ at a yield of 89%.

Example 13

Synthesis of Compound (F$_2$ppy)$_2$Ir(BOZNBOZ)Ir(F$_2$ppy)$_2$

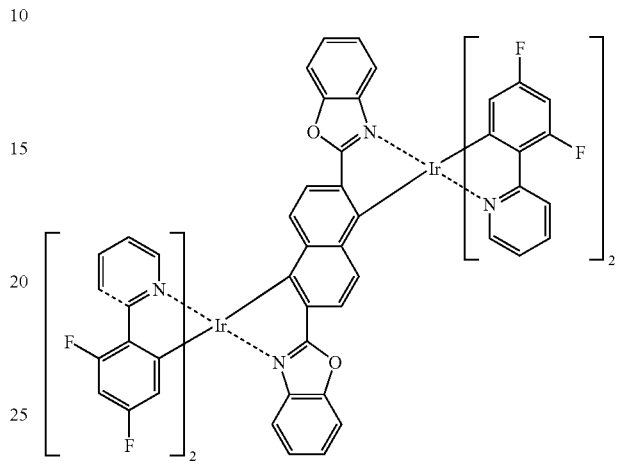

Synthesis of (F$_2$ppy)$_2$Ir(Cl)$_2$Ir(F$_2$ppy)$_2$: 5 mmol of F$_2$ ppy and 10 mmol of IrCl$_3$×H$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce (F$_2$ppy)$_2$Ir(Cl)$_2$Ir(F$_2$ppy)$_2$ at a yield of 92%.

Synthesis of (F$_2$ppy)$_2$Ir(BOZNBOZ)Ir(F$_2$ppy)$_2$: 5 mmol of (F$_2$ppy)$_2$Ir(Cl)$_2$Ir(F$_2$ppy)$_2$, 25 mmol of 2-(2-(benzo[d]oxazole-2-yl)naphthalene-6-yl)benzo[d]oxazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce (F$_2$ppy)$_2$Ir(BOZNBOZ)Ir(F$_2$ppy)$_2$ at a yield of 88%.

Example 14

Synthesis of Compound (PTPD)$_2$Ir(BOZNBOZ)Ir(PTPD)$_2$

Synthesis of (PTPD)$_2$Ir(Cl)$_2$Ir(PTPD)$_2$: 5 mmol of PTPD and 10 mmol of IrCl$_3$×H$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce (PTPD)$_2$Ir(Cl)$_2$Ir(PTPD)$_2$ at a yield of 90%.

Synthesis of (PTPD)$_2$Ir(BOZNBOZ)Ir(PTPD)$_2$: 5 mmol of (PTPD)$_2$Ir(Cl)$_2$Ir(PTPD)$_2$, 25 mmol of 2-(2-(benzo[d]oxazole-2-yl)naphthalene-6-yl)benzo[d]oxazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce (PTPD)$_2$Ir(BOZNBOZ)Ir(PTPD)$_2$ at a yield of 87%.

Example 15

Synthesis of Compound (DMFIQ)$_2$Ir(BOZNBOZ)Ir(DMFIQ)$_2$

Synthesis of (DMFIQ)$_2$Ir(Cl)$_2$Ir(DMFIQ)$_2$: 5 mmol of DMFIQ and 10 mmol of IrCl$_3$×H$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce (DMFIQ)$_2$Ir(Cl)$_2$Ir(DMFIQ)$_2$ at a yield of 88%.

Synthesis of (DMFIQ)$_2$Ir(BOZNBOZ)Ir(DMFIQ)$_2$: 5 mmol of (DMFIQ)$_2$Ir(Cl)$_2$Ir(DMFIQ)$_2$, 25 mmol of 2-(2-(benzo[d]oxazole-2-yl)naphthalene-6-yl)benzo[d]oxazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce (DMFIQ)$_2$Ir(BOZNBOZ)Ir(DMFIQ)$_2$ at a yield of 84%.

Example 16

Synthesis of Compound (PBOZ)$_2$Ir(BTZNBTZ1)Ir(PBOZ)$_2$

Synthesis of 1,2-(benzo[d]thiazole-2-yl)naphthalene-6-yl) benzo[d]thiazole (BTZNBTZ) polyphosphoric acid (125 cm$^3$) was heated at 70° C. for 1 hour while agitating. 0.1 mol of naphthalene-2,6-dicarboxylic acid was added and the resulting mixture was stirred for 15 minutes. 0.2 mol of 2-aminothiophenol was added in a dropwise fashion for 10 minutes. The temperature of the mixture was increased to 150° C. and then this temperature was maintained for 2 hours. The mixture was stirred to cool down to a room temperature. The resulting reaction mixture was stirred for 1 hour with ice water (1.5 dm3), and neutralized with a diluted sodium carbonate hydrate solution. Then it was filtered and dried in an oven for 1 day. The solid was crystallized from dimethylformamide (200 cm$^3$). The final filtered product was rinsed with methanol (100 cm$^3$) and then dried in a 100° C. vacuum oven. As a result, colorless needle-shaped crystalline 1,2-(benzo[d] thiazole-2-yl)naphthalene-6-yl)benzo[d]thiazole was produced at a yield of 71%.

Synthesis of (PBOZ)$_2$Ir(Cl)$_2$Ir(PBOZ)$_2$: 5 mmol of PBOZ and 10 mmol of IrCl$_3$×H$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce (PBOZ)$_2$Ir(Cl)$_2$Ir(PBOZ)$_2$ at a yield of 90%.

Synthesis of (PBOZ)$_2$Ir(BTZNBTZ1)Ir(PBOZ)$_2$: 5 mmol of (PBOZ)$_2$Ir(Cl)$_2$IrPBOZ)$_2$, 25 mmol of 1,2-(benzo[d]thiazole-2-yl)naphthalene-6-yl)benzo[d]thiazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce (PBOZ)$_2$Ir(BTZNBTZ1)Ir(PBOZ)$_2$ at a yield of 86%.

Example 17

Synthesis of Compound (PBTZ)$_2$Ir(BTZNBTZ1)Ir(PBTZ)$_2$

Synthesis of (PBTZ)$_2$Ir(Cl)$_2$Ir(PBTZ)$_2$: 5 mmol of PBOZ and 10 mmol of IrCl$_3$×H$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce (PBTZ)$_2$Ir(Cl)$_2$Ir(PBTZ)$_2$ at a yield of 88%.

Synthesis of (PBTZ)$_2$Ir(BTZNBTZ1)Ir(PBTZ)$_2$: 5 mmol of (PBTZ)$_2$Ir(Cl)$_2$IrPBTZ)$_2$, 25 mmol of 1,2-(benzo[d]thiazole-2-yl)naphthalene-6-yl)benzo[d]thiazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce (PBTZ)$_2$Ir(BTZNBTZ1)Ir(PBTZ)$_2$ at a yield of 82%.

Example 18

Synthesis of Compound (DFPPD)$_2$Ir(BTZNBTZ1)Ir(DFPPD)$_2$

Synthesis of (F$_2$ppy)$_2$Ir(Cl)$_2$Ir(F$_2$ppy)$_2$: 5 mmol of F$_2$ ppy and 10 mmol of IrCl$_3$×H$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce (F$_2$ppy)$_2$Ir(Cl)$_2$Ir(F$_2$ppy)$_2$ at a yield of 94%.

Synthesis of (F$_2$ppy)$_2$Ir(BTZNBTZ1)Ir(F$_2$ppy)$_2$: 5 mmol of (F$_2$ppy)$_2$Ir(Cl)$_2$Ir(F$_2$ppy)$_2$: 25 mmol of 1,2-(benzo[d]thiazole-2-yl)naphthalene-6-yl)benzo[d]thiazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce (F$_2$ppy)$_2$Ir(BTZNBTZ1)Ir(F$_2$ppy)$_2$ at a yield of 90%.

Example 19

Synthesis of Compound (PTPD)$_2$Ir(BTZNBTZ1)Ir(PTPD)$_2$

Synthesis of (PTPD)$_2$Ir(Cl)$_2$Ir(PTPD)$_2$: 5 mmol of PTPD and 10 mmol of IrCl$_3$×H$_2$O were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce (PTPD)$_2$Ir(Cl)$_2$Ir(PTPD)$_2$ at a yield of 90%.

Synthesis of (PTPD)$_2$Ir(BTZNBTZ1)Ir(PTPD)$_2$: 5 mmol of (PTPD)$_2$Ir(Cl)$_2$Ir(PTPD)$_2$, 25 mmol of 1,2-(benzo[d]thiazole-2-yl)naphthalene-6-yl)benzo[d]thiazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce $(PTPD)_2Ir(BTZNBTZ1)Ir(PTPD)_2$ at a yield of 86%.

Example 20

Synthesis of Compound $(DMFIQ)_2Ir(BTZNBTZ1)Ir(DMFIQ)_2$

Synthesis of $(DMFIQ)_2Ir(Cl)_2Ir(DMFIQ)_2$: 5 mmol of DMFIQ and 10 mmol of $IrCl_3 \times H_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce $(DMFIQ)_2Ir(Cl)_2Ir(DMFIQ)_2$ at a yield of 88%.

Synthesis of $(DMFIQ)_2Ir(BTZNBTZ1)Ir(DMFIQ)_2$: 5 mmol of $(DMFIQ)_2Ir(Cl)_2Ir(DMFIQ)_2$, 25 mmol of 1,2-(benzo[d]thiazole-2-yl)naphthalene-6-yl)benzo[d]thiazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce $(DMFIQ)_2Ir(BTZNBTZ1)Ir(DMFIQ)_2$ at a yield of 84%.

Example 21

Synthesis of Compound $(PBOZ)_2Ir(FM_2BTZPBTZ)Ir(PBOZ)_2$

Synthesis of 5-(trifluoromethyl)-2-(4-(trifluoromethyl)benzo[d]thiazole-2-yl)phenyl)benzo[d]thiazole $(FM_2BTZPBTZ)$: polyphosphoric acid (125 cm$^3$) was heated at 70° C. for 1 hour while agitating. 0.1 mol of terephthalic acid was added and the resulting mixture was stirred for 15 minutes. 0.2 mol of 2-amino-4-(trifluoromethyl)benzene thiol was added in a dropwise fashion for 10 minutes. The temperature of the mixture was increased to 150° C. and then this temperature was maintained for 2 hours. The mixture was stirred to cool down to a room temperature. The resulting reaction mixture was stirred for 1 hour with ice water (1.5 dm3), and neutralized with a diluted sodium carbonate hydrate solution. Then it was filtered and dried in an oven for 1 day. The solid was crystallized from dimethylformamide (200 cm$^3$). The final filtered product was rinsed with methanol (100 cm$^3$) and then dried in a 100° C. vacuum oven. As a result, colorless needle-shaped crystalline 5-(trifluoromethyl)-2-(4-(trifluoromethyl)benzo[d]thiazole-2-yl)phenyl)benzo[d]thiazole was produced at a yield of 78%.

Synthesis of $(PBOZ)_2Ir(Cl)_2Ir(PBOZ)_2$: 5 mmol of 2-phenylbenzooxazole (PBOZ) and 10 mmol of $IrCl_3 \times H_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce $(PBOZ)_2Ir(Cl)_2Ir(PBOZ)_2$ at a yield of 92%.

Synthesis of $(PBOZ)_2Ir(FM_2BTZPBTZ)Ir(PBOZ)_2$: 5 mmol of $(PBOZ)_2Ir(Cl)_2IrPBOZ)_2$, 25 mmol of 5-(trifluoromethyl)-2-(4-(trifluoromethyl)benzo[d]thiazole-2-yl)phenyl)benzo[d]thiazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce $(PBOZ)_2Ir(FM_2BTZPBTZ)Ir(PBOZ)_2$ at a yield of 91%.

Example 22

Synthesis of Compound $(PBOZ)_2Ir(FM_2BOZPBOZ)Ir(PBOZ)_2$

Synthesis of 5-(trifluoromethyl)-2-(4-(trifluoromethyl)benzo[d]oxazole-2-yl)phenyl)benzo[d]oxazole polyphosphoric acid (125 cm$^3$) was heated at 70° C. for 1 hour while agitating. 0.1 mol of terephthalic acid was added and the resulting mixture was stirred for 15 minutes. 0.2 mol of 2-amino-4-(trifluoromethyl)phenol was added in a dropwise fashion for 10 minutes. The temperature of the mixture was increased to 150° C. and then this temperature was maintained for 2 hours.

The mixture was stirred to cool down to a room temperature. The resulting reaction mixture was stirred for 1 hour with ice water (1.5 dm3), and neutralized with a diluted sodium carbonate hydrate solution. Then it was filtered and dried in an oven for 1 day. The solid was crystallized from dimethylformamide (200 cm$^3$). The final filtered product was rinsed with methanol (100 cm$^3$) and then dried in a 100° C. vacuum oven. As a result, colorless needle-shaped crystalline 5-(trifluoromethyl)-2-(4-(trifluoromethyl)benzo[d]oxazole-2-yl)phenyl)benzo[d]oxazole was produced at a yield of 78%.

*2-phenylbenzooxazole (PBOZ)

Synthesis of $(PBOZ)_2Ir(Cl)_2Ir(PBOZ)_2$: 5 mmol of 2-phenylbenzooxazole (PBOZ) and 10 mmol of $IrCl_3 \times H_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce $(PBOZ)_2Ir(Cl)_2Ir(PBOZ)_2$ at a yield of 92%.

Synthesis of $(PBOZ)_2Ir(FM_2BOZPBOZ)Ir(PBOZ)_2$: 5 mmol of $(PBOZ)_2Ir(Cl)_2IrPBOZ)_2$, 25 mmol of 5-(trifluoromethyl)-2-(4-(trifluoromethyl)benzo[d]oxazole-2-yl)phenyl)benzo[d]oxazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce $(PBOZ)_2Ir(FM_2BOZPBOZ)Ir(PBOZ)_2$ at a yield of 91%.

Example 23

Synthesis of $(PBTZ)_2Ir(Cl)_2Ir(PBTZ)_2$: 5 mmol of 2-phenylbenzo thiazole (PBTZ) and 10 mmol of $IrCl_3 \times H_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce $(PBTZ)_2Ir(Cl)_2Ir(PBTZ)_2$ at a yield of 92%.

Synthesis of $(PBTZ)_2Ir(FM_2BTZPBTZ)Ir(PBTZ)_2$: 5 mmol of $(PBTZ)_2Ir(Cl)_2IrPBTZ)_2$, 25 mmol of 5-(trifluoromethyl)-2-(4-(trifluoromethyl)benzo[d]thiazole-2-yl)phenyl)benzo[d]thiazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce $(PBTZ)_2Ir(FM_2BTZPBTZ)Ir(PBTZ)_2$ at a yield of 91%.

Example 24

Synthesis of $(PBTZ)_2Ir(Cl)_2Ir(PBTZ)_2$: 5 mmol of 2-phenylbenzo thiazole (PBTZ) and 10 mmol of $IrCl_3 \times H_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce $(PBTZ)_2Ir(Cl)_2Ir(PBTZ)_2$ at a yield of 92%.

Synthesis of $(PBTZ)_2Ir(FM_2BOZPBOZ)Ir(PBTZ)_2$: 5 mmol of $(PBTZ)_2Ir(Cl)_2IrPBTZ)_2$, 25 mmol of 5-(trifluoromethyl)-2-(4-(trifluoromethyl)benzo[d]oxazole-2-yl)phenyl)benzo[d]oxazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce $(PBTZ)_2Ir(FM_2BOZPBOZ)Ir(PBTZ)_2$ at a yield of 91%.

Example 25

Synthesis of $(F_2ppy)_2Ir(Cl)_2Ir(F_2ppy)_2$: 5 mmol of 3,5-difluoro-2-2 phenylpyridine($F_2ppy$) and 10 mmol of $IrCl_3 \times H_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce $(F_2ppy)_2Ir(Cl)_2Ir(F_2ppy)_2$ at a yield of 92%.

Synthesis of $(F_2ppy)_2Ir(FM_2BTZPBTZ)Ir(F_2ppy)_2$: 5 mmol of $(F_2ppy)_2Ir(Cl)_2Ir(F_2ppy)_2$, 25 mmol of 5-(trifluoromethyl)-2-(4-(trifluoromethyl)benzo[d]thiazole-2-yl)phenyl)benzo[d]thiazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce $(F_2ppy)_2Ir(FM_2BTZPBTZ)Ir(F_2ppy)_2$ at a yield of 91%.

Example 26

Synthesis of $(F_2ppy)_2Ir(Cl)_2Ir(F_2ppy)_2$: 5 mmol of 3,5-difluoro-2-2 phenylpyridine($F_2ppy$) and 10 mmol of $IrCl_3 \times H_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce $(F_2ppy)_2Ir(Cl)_2Ir(F_2ppy)_2$ at a yield of 92%.

Synthesis of $(F_2ppy)_2Ir(FM_2BOZPBOZ)Ir(F_2ppy)_2$: 5 mmol of $(F_2ppy)_2Ir(Cl)_2Ir(F_2ppy)_2$, 25 mmol of 5-(trifluoromethyl)-2-(4-(trifluoromethyl)benzo[d]oxazole-2-yl)phenyl)benzo[d]oxazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce $(F_2ppy)_2Ir(FM_2BOZPBOZ)Ir(F_2ppy)_2$ at a yield of 91%.

Example 27

Synthesis of $(PTPD)_2Ir(Cl)_2Ir(PTPD)_2$: 5 mmol of 2-paratolylpyridine (PTPD) and 10 mmol of $IrCl_3 \times H_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce $(PTPD)_2Ir(Cl)_2Ir(PTPD)_2$ at a yield of 92%.

Synthesis of $(PTPD)_2Ir(FM_2BTZPBTZ)Ir(PTPD)_2$: 5 mmol of $(PTPD)_2Ir(Cl)_2Ir(PTPD)_2$, 25 mmol of 5-(trifluoromethyl)-2-(4-(trifluoromethyl)benzo[d]thiazole-2-yl)phenyl)benzo[d]thiazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce $(PTPD)_2Ir(FM_2BTZPBTZ)Ir(PTPD)_2$ at a yield of 91%.

Example 28

Synthesis of $(PTPD)_2Ir(Cl)_2Ir(PTPD)_2$: 5 mmol of 2-paratolylpyridine (PTPD) and 10 mmol of $IrCl_3 \times H_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce $(PTPD)_2Ir(Cl)_2Ir(PTPD)_2$ at a yield of 92%.

Synthesis of $(PTPD)_2Ir(FM_2BOZPBOZ)Ir(PTPD)_2$: 5 mmol of $(PTPD)_2Ir(Cl)_2Ir(PTPD)_2$, 25 mmol of 5-(trifluoromethyl)-2-(4-(trifluoromethyl)benzo[d]oxazole-2-yl)phenyl)benzo[d]oxazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce $(PTPD)_2Ir(FM_2BOZPBOZ)Ir(PTPD)_2$ at a yield of 91%.

Example 29

Synthesis of $(DMFIQ)_2Ir(Cl)_2Ir(DMFIQ)_2$: 5 mmol of 1-(9,9-dimethyl-9H-fluorene-7yl)isoquinoline (DMFIQ) and 10 mmol of $IrCl_3 \times H_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce $(DMFIQ)_2Ir(Cl)_2Ir(DMFIQ)_2$ at a yield of 92%.

Synthesis of $(DMFIQ)_2Ir(FM_2BTZPBTZ)Ir(DMFIQ)_2$: 5 mmol of $(DMFIQ)_2Ir(Cl)_2Ir(DMFIQ)_2$, 25 mmol of 5-(trifluoromethyl)-2-(4-(trifluoromethyl)benzo[d]thiazole-2-yl)phenyl)benzo[d]thiazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce $(DMFIQ)_2Ir$ $(FM_2BTZPBTZ)Ir(DMFIQ)_2$ at a yield of 91%.

Example 30

Synthesis of $(DMFIQ)_2Ir(Cl)_2Ir(DMFIQ)_2$: 5 mmol of 1-(9,9-dimethyl-9H-fluorene-7-yl)isoquinoline (DMFIQ) and 10 mmol of $IrCl_3 \times H_2O$ were dissolved in 100 mL of 2-ethoxyethanol, and refluxed for 24 hours under a nitrogen atmosphere. The solution was cooled down to room temperature, and 200 mL of 5% hydrochloric acid aqueous solution was added to the solution for eduction, filtered, rinsed with water and an ether solvent, and dried to thereby produce $(DMFIQ)_2Ir(Cl)_2Ir(DMFIQ)_2$ at a yield of 92%.

Synthesis of $(DMFIQ)_2Ir(FM_2BOZPBOZ)Ir(DMFIQ)_2$: 5 mmol of $(DMFIQ)_2Ir(Cl)_2Ir(DMFIQ)_2$, 25 mmol of 5-(trifluoromethyl)-2-(4-(trifluoromethyl)benzo[d]oxazole-2-yl) phenyl)benzo[d]oxazole, and 50 mmol of potassium carbonate were mixed in 100 mL of 1,2-dichloroethane, and refluxed for 24 hours under a nitrogen atmosphere. After the reaction was complete, the solution was cooled down to about 50° C., and filtered. The filtrate solution was purified by using column chromatography to thereby produce $(DMFIQ)_2Ir$ $(FM_2BOZPBOZ)Ir(DMFIQ)_2$ at a yield of 91%.

PL spectra of the above chemical compounds were acquired and the results were presented in the following Table 1.

TABLE 1

| compound | yield | PL (nm) |
|---|---|---|
| compound 1 | 88% | 597 |
| compound 2 | 91% | 573 |
| compound 3 | 80% | 570 |
| compound 4 | 87% | 576 |
| compound 5 | 75% | 572 |
| compound 6 | 88% | 602 |
| compound 7 | 84% | 595 |
| compound 8 | 85% | 593 |
| compound 9 | 90% | 596 |
| compound 10 | 91% | 594 |
| compound 11 | 84$ | 582 |
| compound 12 | 83% | 587 |
| compound 13 | 87% | 577 |
| compound 14 | 81% | 579 |
| compound 15 | 78% | 569 |
| compound 16 | 79% | 558 |
| compound 17 | 77% | 552 |
| compound 18 | 80% | 551 |
| compound 19 | 80% | 554 |
| compound 20 | 84% | 547 |
| compound 21 | 82% | 541 |
| compound 22 | 80% | 545 |
| compound 23 | 76% | 540 |
| compound 24 | 75% | 604 |
| compound 25 | 86% | 594 |
| compound 26 | 90% | 596 |
| compound 27 | 86% | 597 |
| compound 28 | 88% | 576 |
| compound 29 | 75% | 573 |
| compound 30 | 78% | 577 |

Example 31

As for an anode, a 10 $\Omega/cm^2$ ITO substrate produced by the Corning Company was used. A hole injection layer was formed in a thickness of 60 nm by depositing IDE406 on top of the substrate in a vacuum condition. Subsequently, a hole transport layer was formed by depositing TPD chemical compound on top of the hole injection layer in a thickness of 30 nm in a vacuum condition. A light emitting layer was formed in a thickness of 20 nm by depositing a transition metal compound on top of the hole transport layer in a vacuum condition.

Subsequently, an HBL layer was formed in a thickness of 5 nm by depositing BCP on top of the light emitting layer in a vacuum condition. An electron transport layer (ETL) was formed in a thickness of 20 nm by depositing Alq3 on top of the light emitting layer in a vacuum condition. An organic electroluminescence device was completed by sequentially depositing LiF 1 nm and Al 300 nm on top of the electron transport layer in a vacuum condition to thereby form a LiF/Al electrode.

Simple modifications and alternations of the present invention can be easily made by the ordinary skilled person in the art within the spirit and scope of the appended claims.

The invention claimed is:

1. A binuclear transition metal compound of the following Chemical Formula 1:

[Chemical Formula 1]

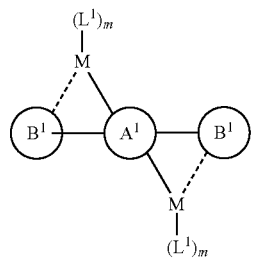

wherein M is a transition metal selected from the group consisting of Ir, Pt, Rh, Re, and Os, m is 2, provided that the m is 1 when M is Pt, $A^1$ and $B^1$ in the above Formula 1 are of the following Formula 3:

[Chemical Formula 3]

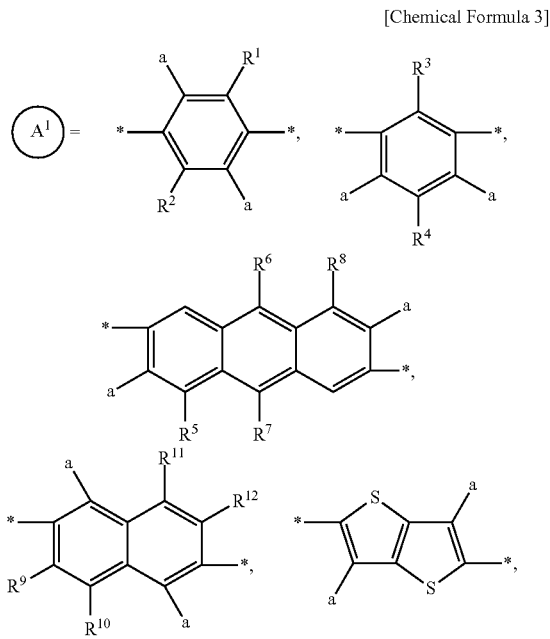

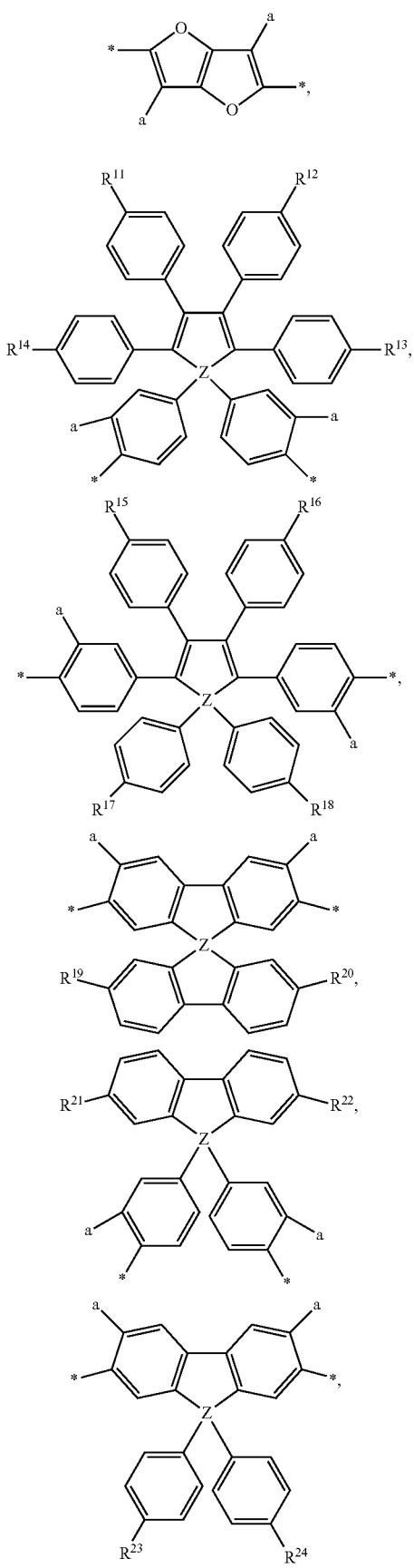

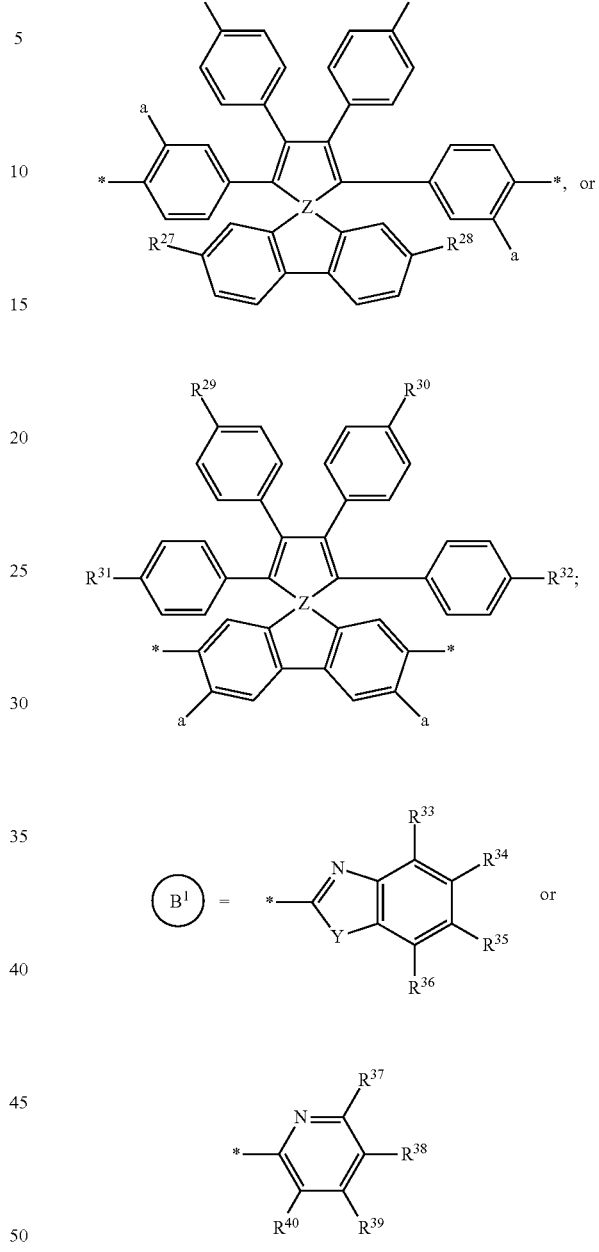

wherein, in the above Formula 3, $A^1$ is bound with a portion denoted as * and adjacent $B^1$ by a covalent bond, and the transition metal, M forms a complex compound by a covalent with a portion denoted as "a" of $A^1$ and by a coordination bond with a N atom of $B^1$, Z is a Si, or C atom, $R^1$-$R^{32}$, $R^{34}$, $R^{35}$, $R^{36}$, $R^{38}$, $R^{39}$, and $R^{40}$ are the same or different, and are substituents selected from the group consisting of hydrogen, a C1 to C20 alkyl, an aryl, a cycloalkyl, a halogen, a trifluoromethyl, carbonyl, vinyl, and acetylenyl, $R^{33}$ and $R^{37}$ are hydrogen, a C1 to C20 alkyl excluding an aromatic cyclic substituent, a cycloalkyl, or a halogen, and $L^1$ is of the following Formula 5:

[Chemical Formula 5]

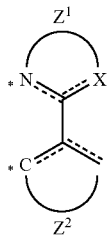

wherein the above Formula 5 is an independent ligand having a covalent bond site with a carbon denoted as * and a coordination bond with nitrogen and forming a complex compound with the transition metal M, and X is a hetero atom selected from the group consisting of nitrogen, oxygen, sulfur, and phosphorus, and $Z^1$ and $Z^2$ are atoms for forming a C4 to C7 aromatic hydrocarbon ring or aromatic heterocyclic ring, and wherein $L^1$ of Chemical Formula 5 is one of the following Chemical Formulae 7:

[Chemical Formulae 7]

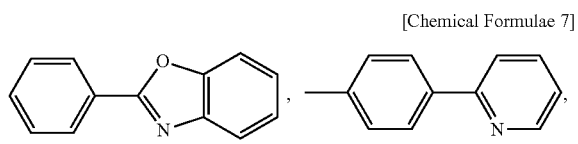

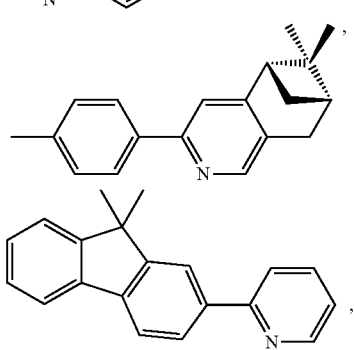

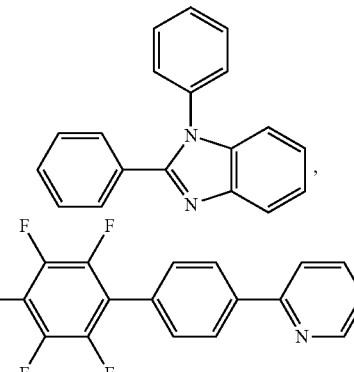

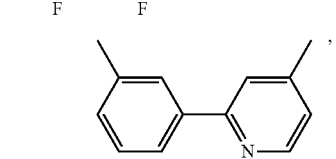

-continued

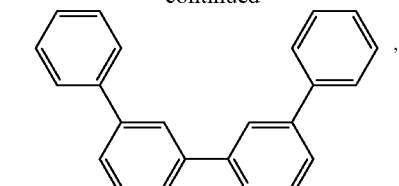

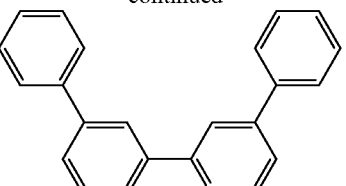

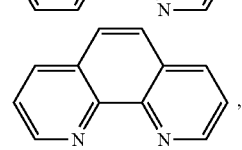

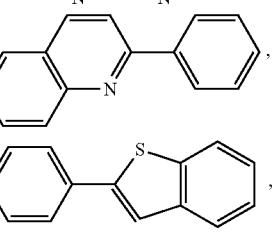

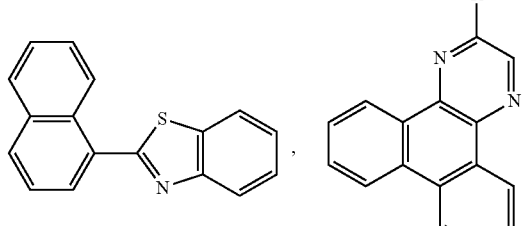

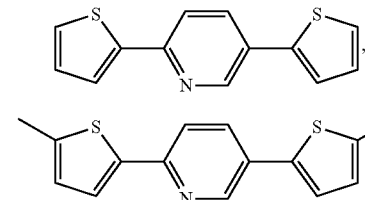

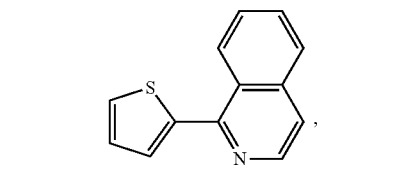

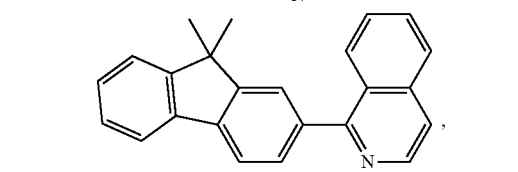

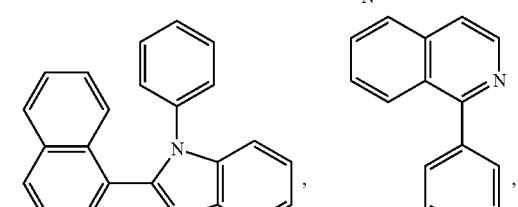

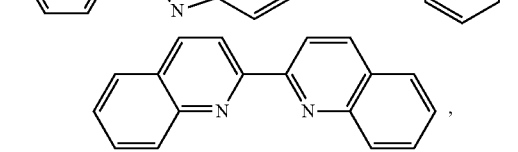

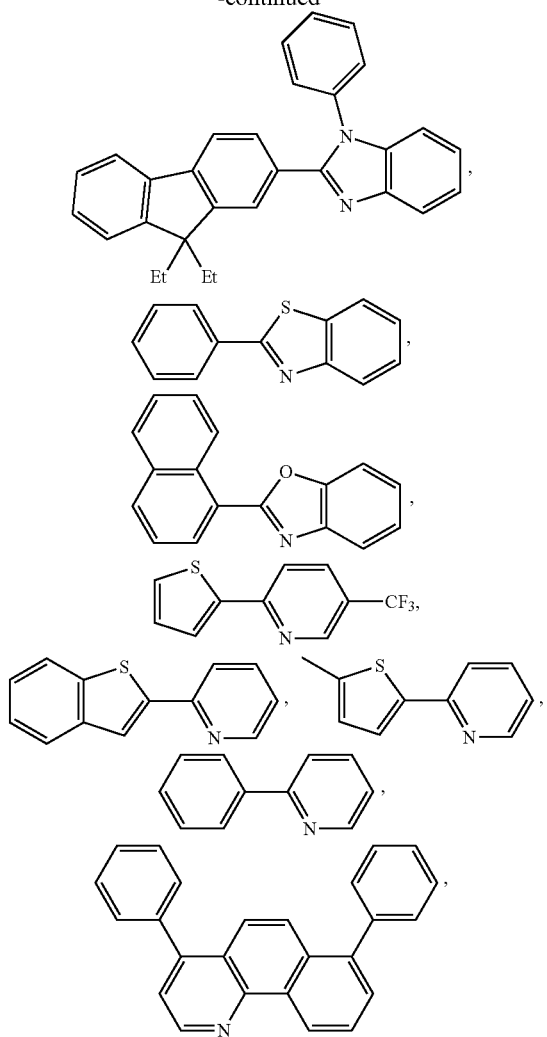
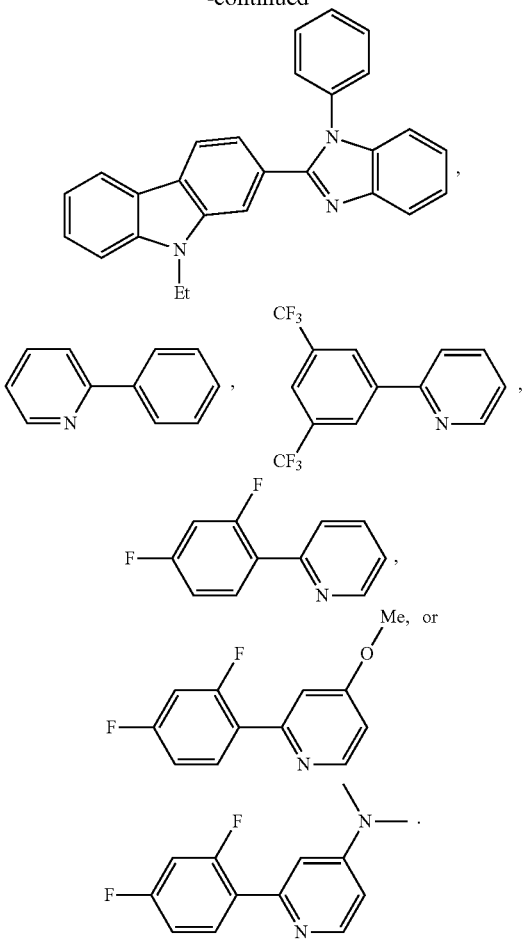
2. An organic electroluminescence device comprising the metal compound of claim 1.
* * * * *